(12) United States Patent
Liu et al.

(10) Patent No.: US 9,506,053 B2
(45) Date of Patent: Nov. 29, 2016

(54) METHODS OF SELECTING BIOLOGIC-PRODUCING CELL LINES BY NEXT GENERATION SEQUENCING

(71) Applicant: AbbVie Inc., North Chicago, IL (US)

(72) Inventors: Junjian Liu, Shrewsbury, MA (US); Dean Regier, Upton, MA (US); Sheng Zhang, Shrewsbury, MA (US); Gerald Carson, Belmont, MA (US); David Ouellette, Sturbridge, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/446,653

(22) Filed: Jul. 30, 2014

(65) Prior Publication Data

US 2015/0038337 A1 Feb. 5, 2015

Related U.S. Application Data

(60) Provisional application No. 61/861,362, filed on Aug. 1, 2013, provisional application No. 61/950,662, filed on Mar. 10, 2014.

(51) Int. Cl.
| | |
|---|---|
| *C12N 15/64* | (2006.01) |
| *C12N 15/10* | (2006.01) |
| *C12Q 1/68* | (2006.01) |
| *C07K 16/00* | (2006.01) |
| *C12N 15/01* | (2006.01) |

(52) U.S. Cl.
CPC .......... *C12N 15/1034* (2013.01); *C07K 16/00* (2013.01); *C12N 15/01* (2013.01); *C12Q 1/6869* (2013.01); *C07K 2317/14* (2013.01)

(58) Field of Classification Search
None
See application file for complete search history.

(56) References Cited

U.S. PATENT DOCUMENTS

| 4,554,101 A | 11/1985 | Hopp |
|---|---|---|
| 2009/0311253 A1 | 12/2009 | Ghayur et al. |

OTHER PUBLICATIONS

Fu et al., J. Chromatography B (2012) vol. 908, pp. 1-8.*
Casales E. et al.; A novel system for the production of high levels of functional human therapeutic proteins in stable cells with a Semliki Forest virus noncytopathic vector, (2010).
Claverol S., et al.; Characterization of Protein Variants and Post-Translational Modifications: ESI-MSn Analyses of Intact Proteins Eluted from Polyacrylamide Gels; Molecular & Cellular Proteomics 2.8; 2003; pp. 483-493.
Davies, S. L. et al. Functional Heterogeneity and Heritability in CHO Cell Populations; Biotechnology and Bioengineering, vol. 110, No. 1, Jan. 2013, pp. 260-274.
Dorai H., et al.; Investigation of Product Microheterogeneity, A Case Study in Rapid Detection of Mutation in Mammalian Production Cell Lines; BioProcess International, Sep. 2007; 5 : 66-75.
Golberg A. & Rubinsky B.; The Effect of Electroporation Type Pulsed Electric Fields on DNA in Aqueous Solution; Technology in Cancer Research and Treatment (2010); vol. 9, No. 4: 423-430.
Goulain M., et al. Methotrexate-induced misincorporation of uracil into DNA; Proc. Natl. Acad. Sci., Apr. 1980; vol. 77, No. 4:1956-1960.
Harris R.J., et al.; Assessing Geneetic Heterogeneity in Production Cell Lines: Detection by Peptide Mapping of a Low Level Tyr to Gln Sequence Variant in a Recombinant Antibody; Nature Biotechnology 1993; 11: 1293-1297.
Kim, N.S. et al., Clonal Variability Within Dihydrofolate Reductase-Mediated Gene Amplified Chinese Hamster Ovary Cells; Stability in the Absence of Selective Pressure; Biotechnology and Bioengineering, vol. 60, No. 6, Dec. 1998, pp. 260-274.
Margulies M., et al.; Genome sequencing in Microfabricated high-density picolitre reactors; Nature 2005; 437: 376-380.
Martin S.A., et al. Methotrexate induces oxidative DNA damage and is selectively lethal to tumour cells with defects in the DNA mismatch repair gene MSH2; EMBO Molecular Medcine 2009; 1: 323-337.
McCulloch S.D. & Kunkel T.A.; The fidelity of DNA synthesis by eukaryotic replicative and translesion synthesis polymerases Cell Research (2008); 18: 148-161.
Metzker M.L.; applications of next-generation sequencing, Sequencing technologies—the next generation; Nature Review, Jan. 2010; 11 : 31-46.
PCT/US2014/048788 International Search Report & Written Opinion mailed Nov. 6, 2014, 10 pages.
Que A.H., et al.; Sequence Variant Analysis Using Peptide Mapping by OLC-MS/MS, Assessing Genetic Heterogeneity in MAb-Producing Cell Lines; BioProcess International, Sep. 2010; pp. 52-60.
Shendure J. & Ji H.; Next-generation DNA sequencing; Nature Biotechnology, Oct. 2008 ; vol. 26, No. 10: 1135-1145.
Shroder J, et al. Predicting DNA-Binding Specificities of Eukaryotic Transcription Factors; PLoS One, Nov. 2010 ; vol. 5; Issue 11, pp. 1-15.
Victoria J.G., et al.; Viral Nucleic Acids in Live-Attenuated Vaccines: Detection of Minority Variants and an Adventitious Virus; Journal of Virology Jun. 2010; vol. 84, No. 12: 6033-6040.
Wan M., et al.; Variant Antibody Identification by Peptide Mapping; Biotechnology and Bioengineering; vol. 62, No. 4, Feb. 1999: 485-488.
Wen D., et al.; Discovery and Investigation of Misincorporation of Serine at Asparagine Positions in Recombinant Proteins Expressed in Chinese Hamster Ovary Cells; J. of Biological Chemistry, Nov. 20, 2009; vol. 284, No. 47: 32686-32694.
Yu X.C., et al.; Identification of Codon-Specific Serine to Asparagine Mistranslation in Recombinant Monoclonal Antibodies by High-Resolution Mass Spectrometry; Analytical Chemistry 2009; 81 : 9282-9290.

* cited by examiner

*Primary Examiner* — Jim Ketter
(74) *Attorney, Agent, or Firm* — Lathrop & Gage LLP; James H. Velema, Esq.

(57) ABSTRACT

An optimized multi-step cell line screening method based on next generation sequencing (NGS) and mass spec (MS) is disclosed. The method helps reduce variants in the biologic-producing cell line and improve the efficiency of cell line development process.

26 Claims, 17 Drawing Sheets

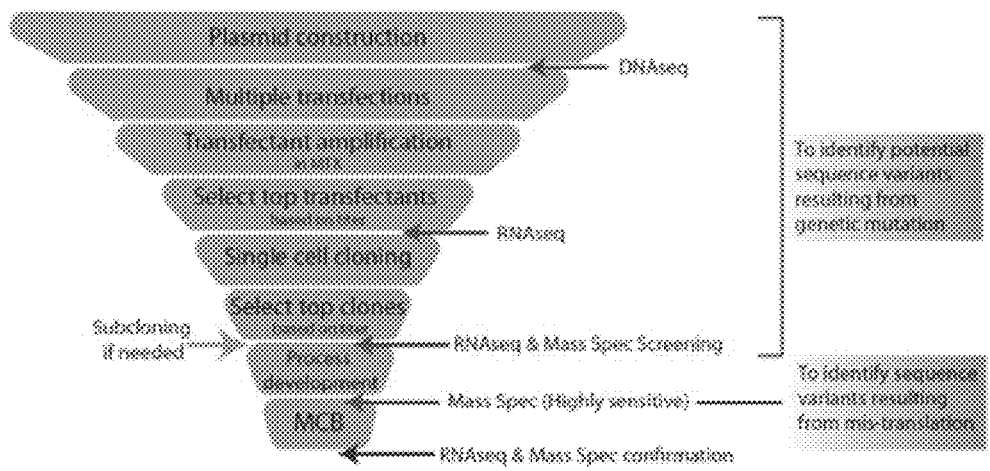
Figure 1. NGS screening to assist and improve cell line development.
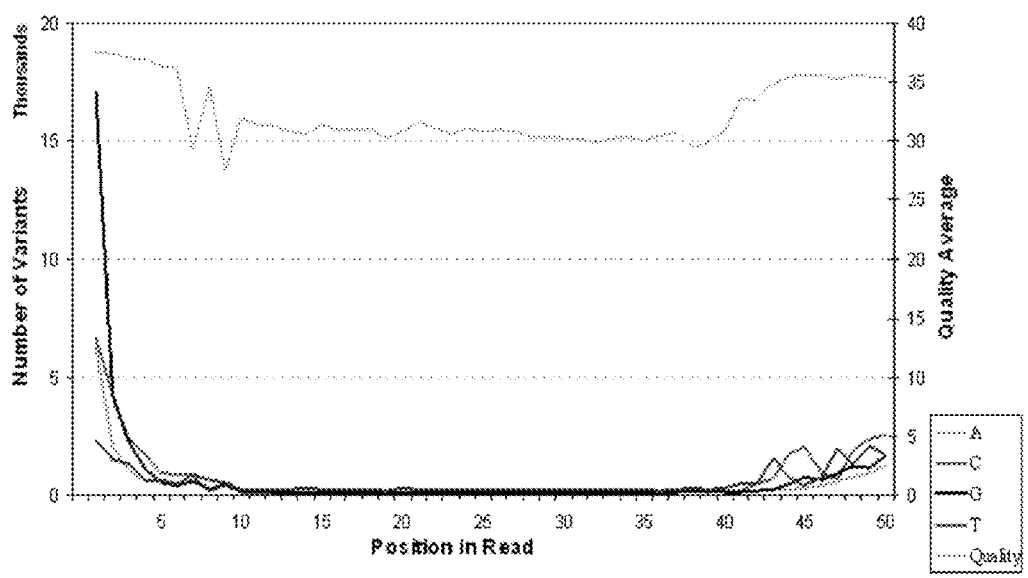
Figure 2. Evaluation of sequencing quality: Variant frequency vs. base position

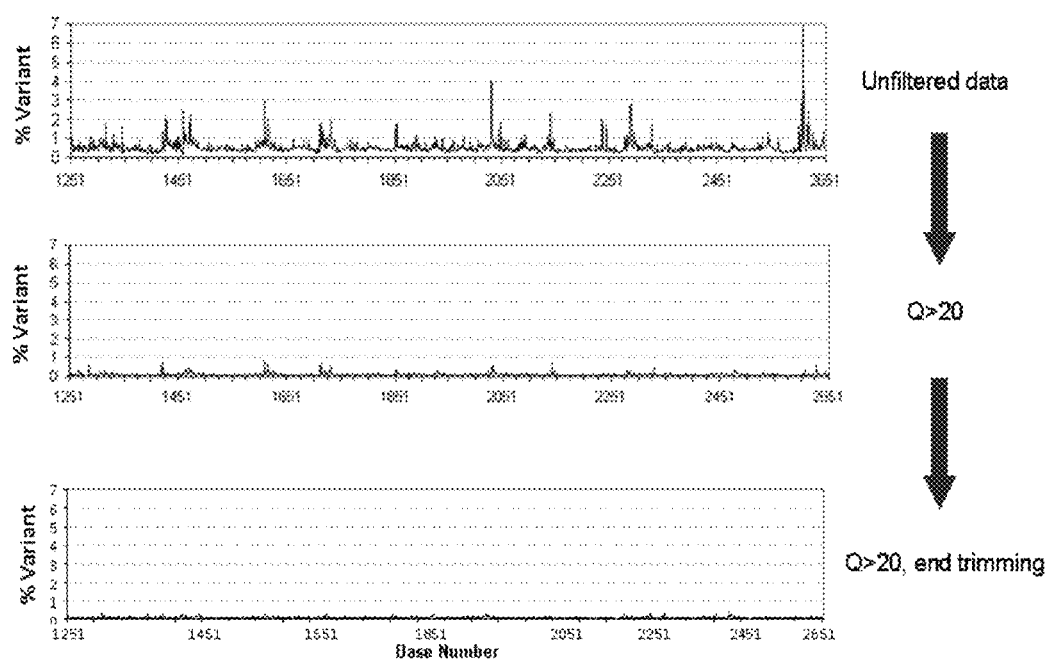
Figure 3. Application of Q value and end-trimming in data analysis

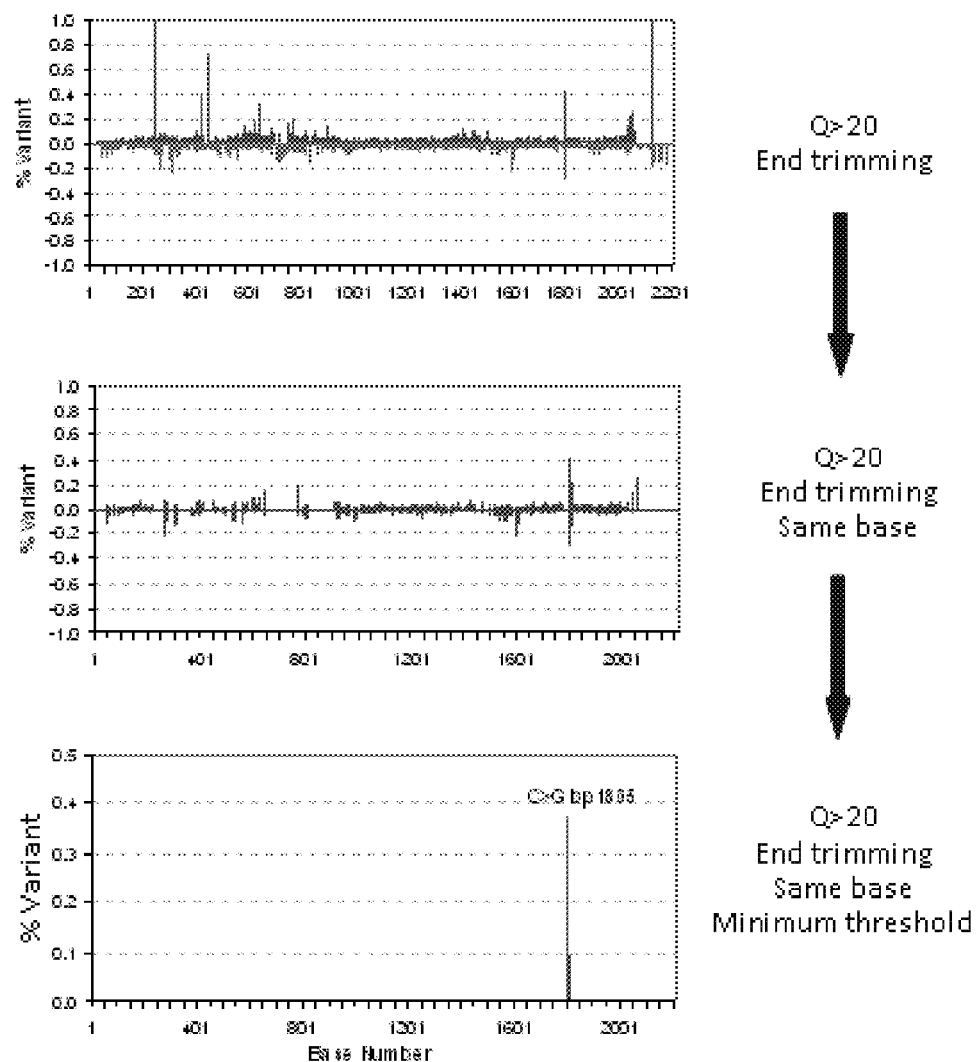
Figure 4. Data analysis with more filters to reduce background.

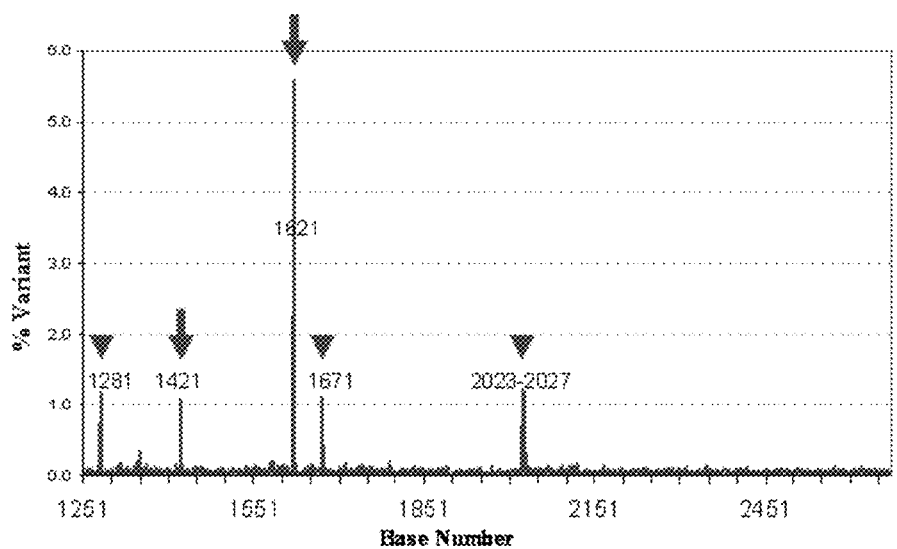
Figure 5. Sequencing data analysis of CHO line A/A-mut virtual mix

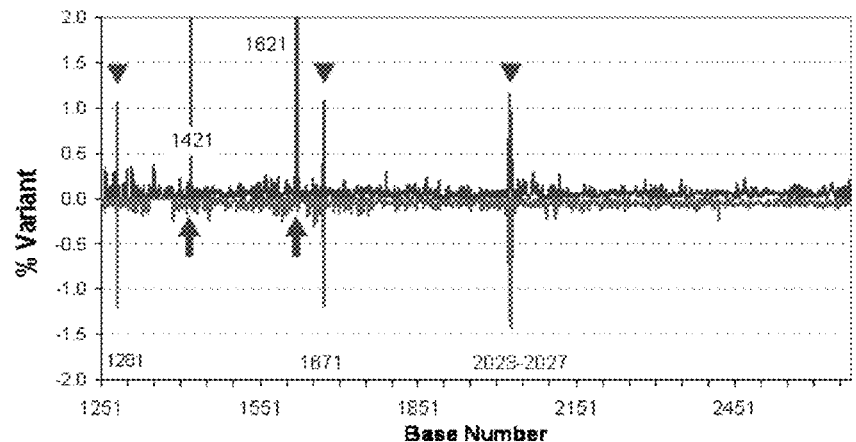
- The artifacts (solid arrows) are the "Solexa Base Calling Errors"
- These sequencing artifacts occur on one strand only
- By contrast, true mutants (triangles) are equally represented by both (+) and (-) strand reads
Figure 6. Sequencing data analysis of CHO line A/A-mut virtual mix
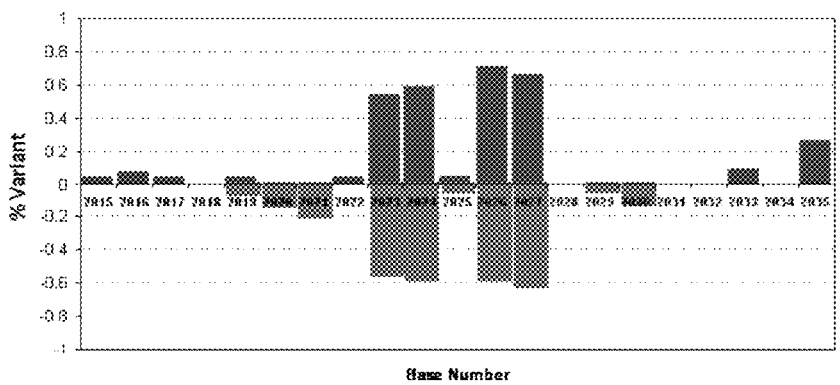
Figure 7. Detection of clustered HC sequence variants in CHO line A/A-mut virtual mix

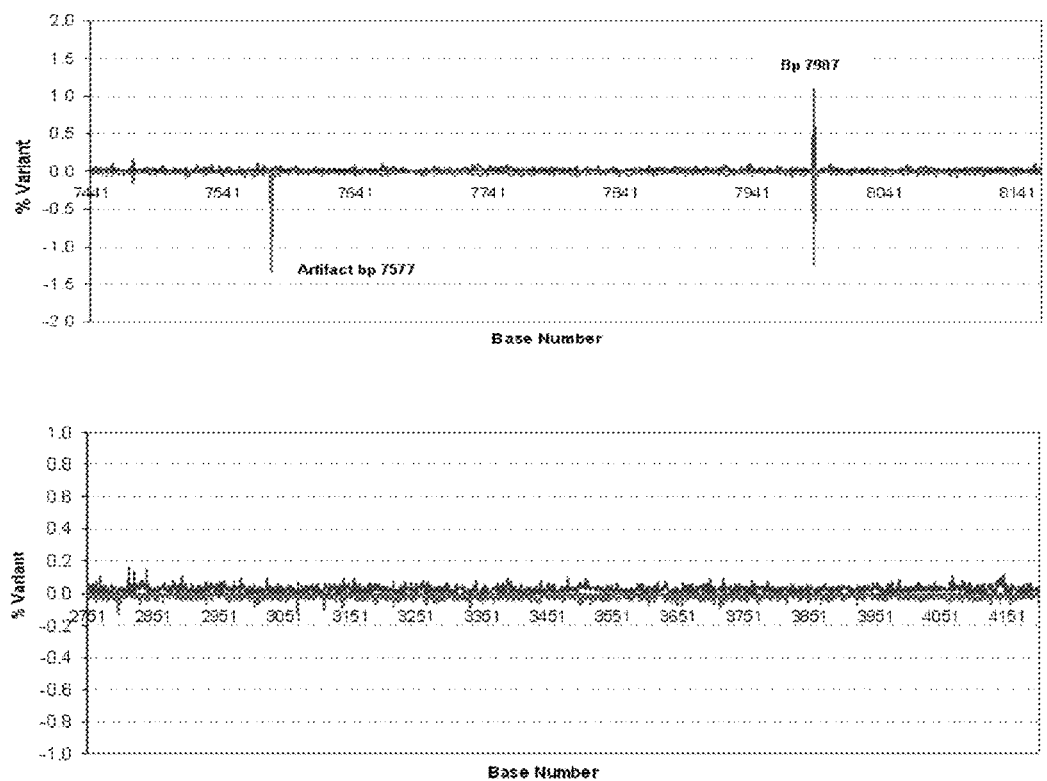
Figure 8. RNAseq analysis of CHO line B LC and HC

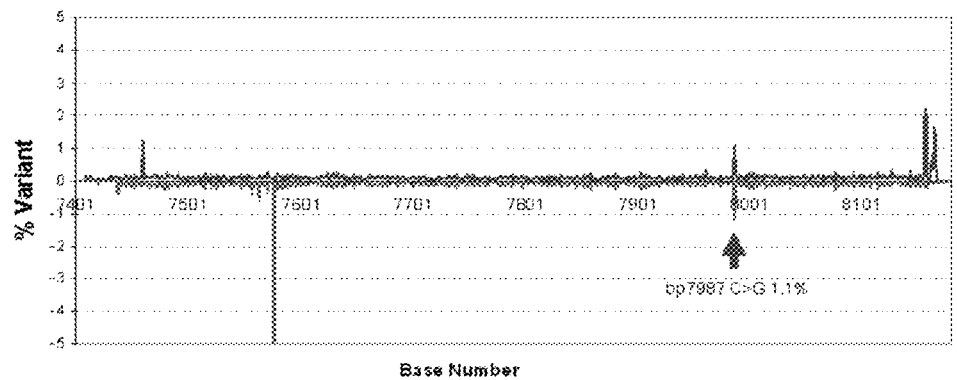
Figure 9. Resequencing of LC RT-PCR product derived from CHO line B
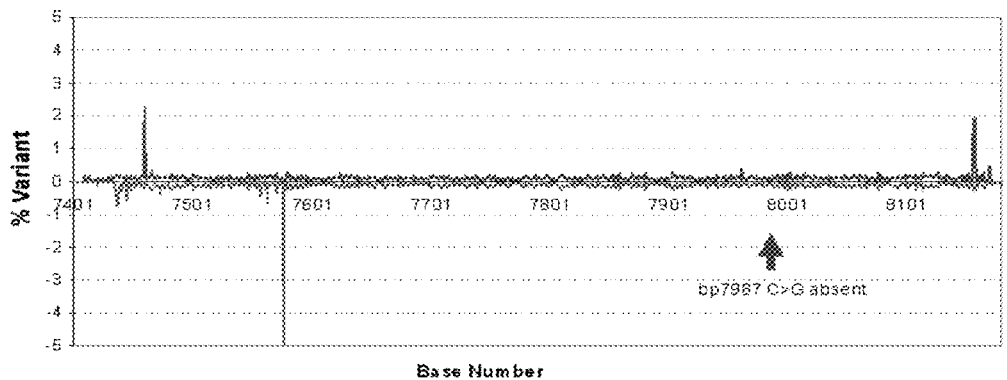
Figure 10. DNAseq analysis of the plasmid used for generating of the CHO line B

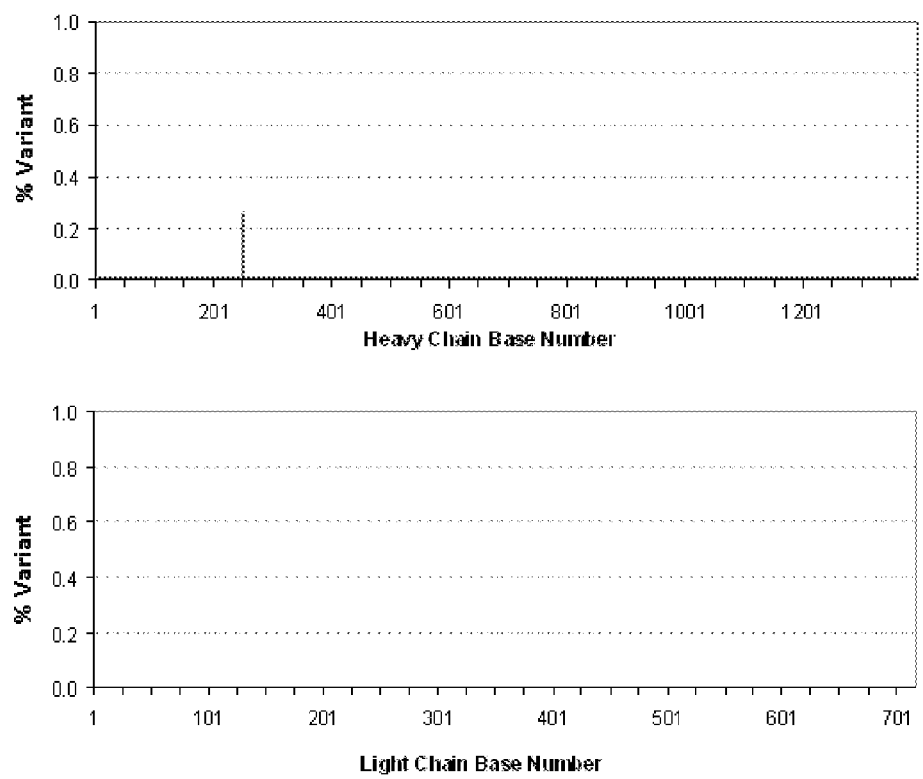
Figure 11. DNAseq analysis of CHO vector for generating of CHO line C.

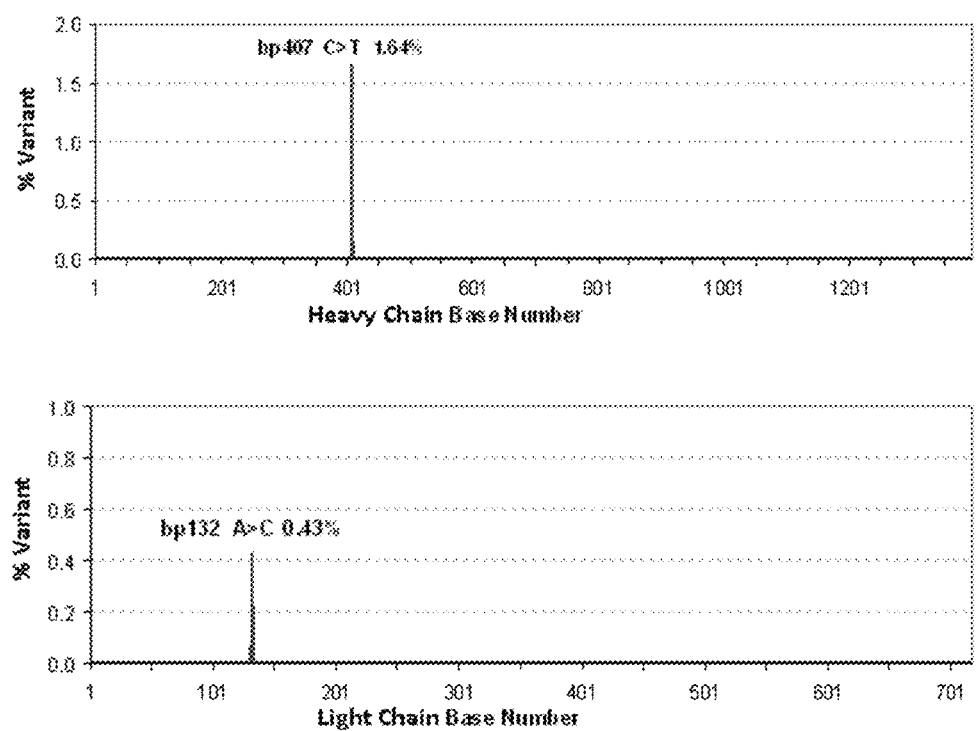
Figure 12. RNAseq analysis of transfection pool #4 for CHO line C.

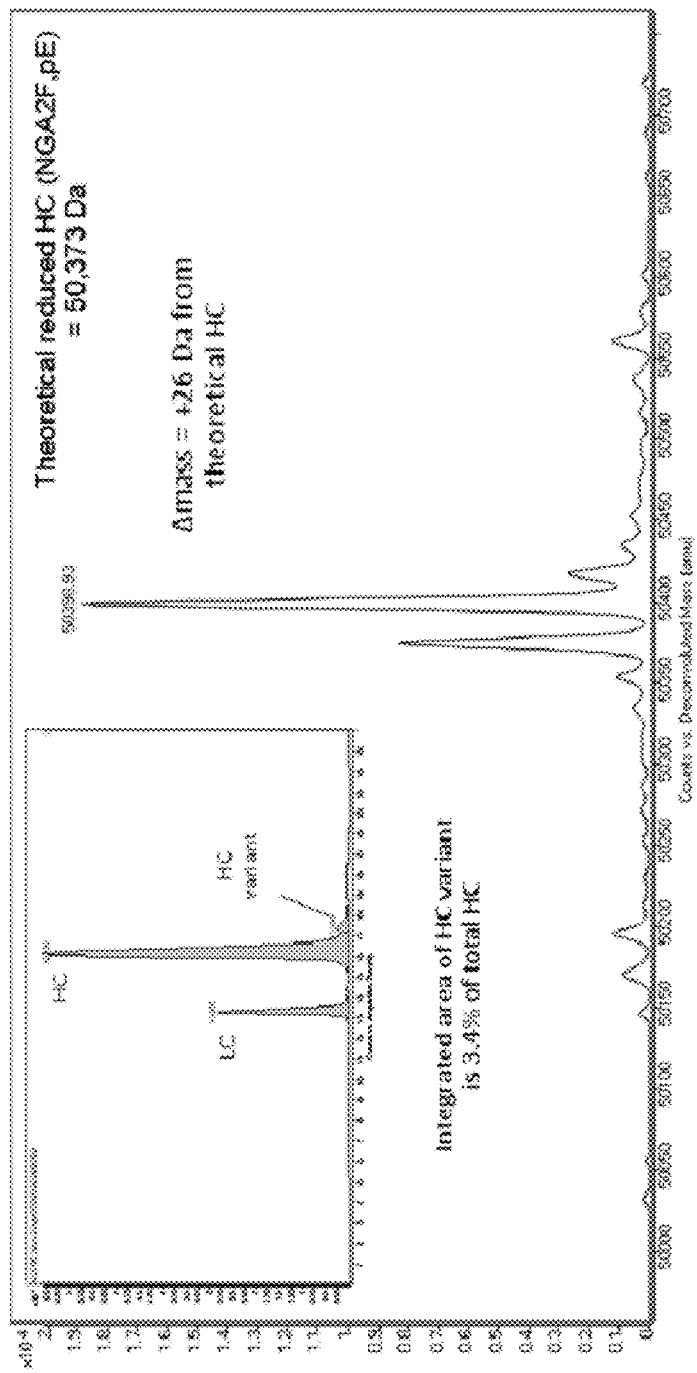
Figure 13. Mass Spectrometry confirmation of the heavy chain mutation of pool #4.

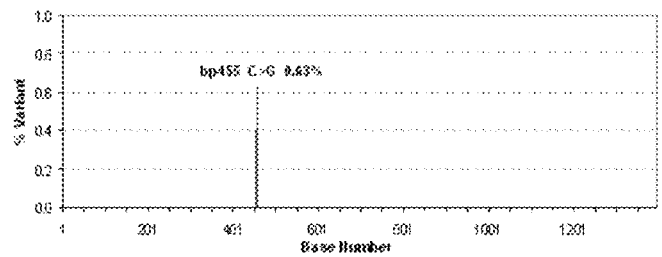
Figure 14. RNAseq analysis of a subclone of CHO line C.
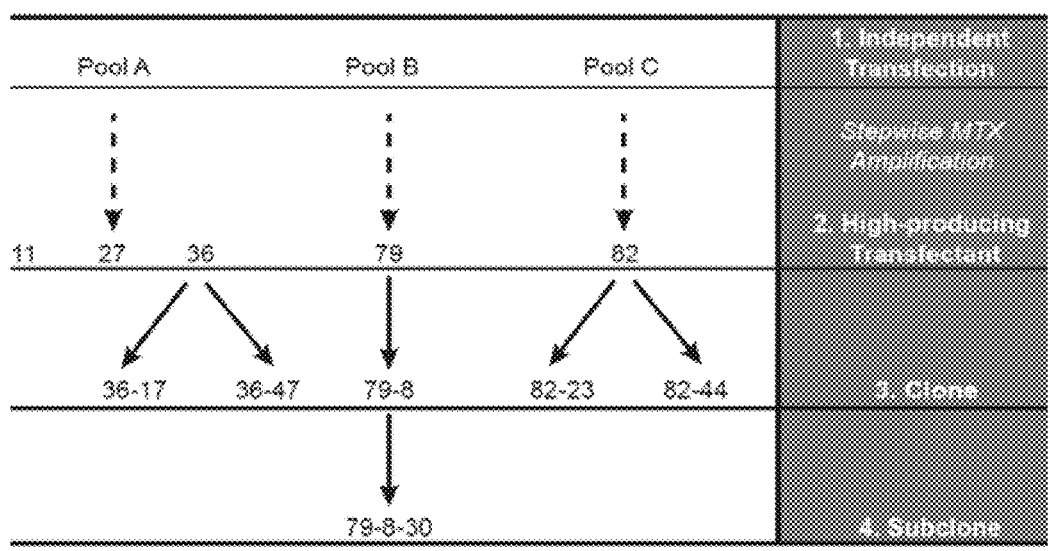
Figure 15

SEQUENCE LISTING

<160> NUMBER OF SEQ ID NOS: 2

<210> SEQ ID NO 1
<211> LENGTH: 24
<212> TYPE: PRT
<213> ORGANISM: Artificial Sequence
<220> FEATURE:
<223> OTHER INFORMATION: antibody heavy chain fragment

<400> SEQUENCE: 1

Ser Glu Ile Thr Thr Glu Phe Asp Tyr Trp Gly Gln Gly Thr Leu Val
1               5                   10                  15

Thr Val Leu Ser Ala Ser Thr Lys
            20

<210> SEQ ID NO 2
<211> LENGTH: 24
<212> TYPE: PRT
<213> ORGANISM: Artificial Sequence
<220> FEATURE:
<223> OTHER INFORMATION: antibody heavy chain fragment

<400> SEQUENCE: 2

Ser Glu Ile Thr Thr Glu Phe Asp Tyr Trp Gly Gln Gly Thr Leu Val
1               5                   10                  15

Thr Val Ser Ser Ala Ser Thr Lys
            20

METHODS OF SELECTING BIOLOGIC-PRODUCING CELL LINES BY NEXT GENERATION SEQUENCING

RELATION APPLICATIONS

This application claims priority to U.S. Provisional Patent Application No. 61/861,362, filed Aug. 1, 2013, and U.S. Provisional Patent Application No. 61/950,662, filed Mar. 10, 2014, both of which are incorporated by reference into the present application in their entirety and for all purposes.

SEQUENCE LISTING

This application is accompanied by a sequence listing in a computer readable form that accurately reproduces the sequences described herein.

FIELD OF THE INVENTION

This disclosure pertains to production of biologics in recombinant cells. More particularly, the disclosure relates to methods for generating and characterizing biologic-producing cell lines.

BACKGROUND

Biologics are a category of medicinal products that are created by biologic processes for therapeutic purpose. Examples of biologics may include vaccines, blood or blood components, allergenics, somatic cells, gene therapies, tissues, therapeutic proteins, and living cells, among others. In most cases, the term "biologics" is used to specifically referred to a class of therapeutics that are produced by means of biological processes involving recombinant DNA technology. For instance, these biologics may include substances that are identical or nearly identical to the body's own key proteins, such as erythropoietin and insulin. Fusion proteins have also been used as biologics. For example, constructs have been used which contain cell surface receptors or other type of proteins linked to the immunoglobulin frame or an immunoglobulin fragment. Another example of biologics is monoclonal antibodies. These antibodies are typically "custom-designed" antibodies that are capable of binding to certain antigens in the body thereby blocking or modifying the unwanted biological function of the antigens.

In order to achieve a consistent efficacy in disease treatment, it is important to maintain a high level of homogeneity in the biologics. However, it is challenging to achieve a high level of homogeneity for biologics because biologic manufacturing is much more complex than traditional chemical synthesis. See e.g., Harris et al. 1993; Wan et al., 1999; Dorai H, et al. 2007; and Wen D, et al., 2009; A number of different technologies have been used to assess heterogeneity of biologics.

Mass spectrometry (MS or mass spec) based methods have been used in detection of sequence variants at the protein level. It has been reported that mass spectrometry (MS)-based peptide mapping was capable of detecting 1% to 27% of a Y376Q variant in a purified anti-Her2 antibody. See Harris et al. 1993. Through subcloning of the anti-Her2 antibody production Chinese hamster ovary (CHO) cell line followed by reverse transcription-polymerase chain reaction (RT-PCR), the authors were able to confirm that 10% of the subclones produced high levels of the Y376Q variant. Claverol and colleagues developed an electrophoresis-MS" method which could efficiently identify protein variants and post-translational modifications. See Claverol, et al., 2003. Using liquid chromatograph-MS/MS, Que et al. reported that 1% or lower of sequence variants in a monoclonal antibody could be detected. See Que et al., 2010.

Although MS-based methods have been reported to be capable of detecting single digit sequence variants, MS-based methods may miss certain type of variants such as unexpected, low-abundance, or variants with same/similar molecular weights. Typically, protein variants have to be isolated and enriched to a high level to achieve sensitive characterization. Moreover, MS-detected variants may not represent true genetic variations.

At the nucleic acid level, Sanger sequencing has traditionally played an important role in detecting sequence variants. In a typical process, the targeted region is amplified by PCR from a DNA template or by RT-PCR from an RNA template, followed by cloning, purification of plasmid clones and sequencing. For low-abundance variants, hundreds or thousands of clones need to be sequenced before a conclusion can be reached. PCR products can also be subject to sequencing directly. However, minor mutations (<30%) cannot be accurately detected. Overall, the process of PCR-cloning-sequencing is laborious and inaccurate in the detection of sequence variants, especially for low-abundance variants.

SUMMARY

This disclosure advances the art by providing methods for generating and/or characterizing biologic-producing cell lines. Many therapeutic biologics, such as proteins, are produced by cultured mammalian cells containing one or more polynucleotides encoding the proteins of interest. In production cell line development, genetic variation may happen spontaneously or in response to changing environment. Mass spec-derived methods have been used to detect these variations. However, mass spec is not ideal for detecting unexpected, low-abundance sequence variants or sequencing variations that do not result in a mass difference. A further limitation of mass spec is that detection of a protein variant does not necessarily reflect a genetic variation, which may be required for developing a stable cell line.

Methodology is disclosed for generating a production cell line capable of producing a protein of interest with relative low or no variants. The methods may include acquiring deep sequencing coverage by next generation sequencing (NGS) for the area of interest. Novel data analysis may then be applied to sensitively detect and quantify point mutations or simple genetic variations which are the most commonly observed undesired events in cell line development. A method to apply real-time next generation sequencing screening is also disclosed, which may be applied in cell line development to improve the cell line development process.

In one embodiment, the method may include the steps: (a) culturing a plurality of cells that contain a polynucleotide encoding the protein of interest; (b) sequencing the polynucleotide by using the next generation sequencing (NGS) techniques; (c) comparing the sequence of the polynucleotide obtained in step (b) with known sequence of the polynucleotide to determine the percentage of sequence variants in the polynucleotide in the cell line; and (d) selecting those cells having less than 2% sequence variants in the polynucleotide for further development into a production cell line capable of producing the protein of interest. In one aspect, the cell line having less than 5%, 4%, 3%, 2%, 1.5%, 1%, 0.5%, or even less than 0.1% of sequence variants in the polynucleotide is selected for further development into a production cell line.

The cell line may be a mammalian cell line, an insect cell line, or of other cell types.

In one embodiment, the polynucleotide may a DNA, an RNA or combination thereof that encodes the protein of interest. In another embodiment, the sequencing in step (b) may be performed by RNAseq to sequence the transcriptome of the cell line.

In another embodiment, the culturing step (a) may include amplification of the cells using a chemical. Such chemicals may include but are not limited to dihydrofolate reductase (DHFR), methotrexate (MTX), glutamine synthetase (GS), methionine sulfoximine (MSX) or combination thereof. In one aspect, MTX may be used for the amplification and may be performed in a stepwise fashion. In another aspect, the amplification may include at least two steps, wherein the first step is conducted at a concentration of from 50 nM to 150 nM of MTX, preferably at about 100 nM MTX, and the second step is conducted at a concentration of from 400 nM to 600 nM of MTX, preferably at about 500 nM MTX. Clones producing the highest amount of the protein of interest may be selected after either or both of the first and second step of amplification for further development. In one aspect, the selected clone may be subject to sequencing to determine the percentage of sequence variants of the DNA and/or RNA encoding the protein of interest in the clone. In another aspect, clones having less than 5%, 4%, 3%, 2%, 1.5%, 1%, 0.5%, or even less than 0.1% of sequence variants in the RNA is selected for further development into a production cell line.

In one aspect, before making a determination that a polynucleotide carries a variant at a particular position, both strands of the polynucleotide are required to have the same base calling. Because base calling errors typically occur in single-strand mismatch, by requiring both strands to have the same base calling, true mutations may be distinguished from those mutations resulting from base calling errors.

The tallied sequence data may be used to calculate the variance at each position of the RefSeq, mean variance and standard deviation for regions of interest, for example, in an open reading frame. The variance is the number of mismatches expressed as percent of total reads covering the position. The mean is the average variance for a region and the standard deviation may be calculated for the same region. Plus and minus strand results are calculated separately. In one aspect, each variant as determined in step (d) is required to be 2 standard deviations above mean before making a determination that a polynucleotide carries a variant at a particular position.

In another aspect, a data filtering process may be employed which determines the data quality at each position by investigating mismatch/variant frequency at each by locations of the short reads. For a high quality data set, the plot typically shows an abundance of mismatches at both ends of the read and a central region with a low and constant rate of variant reporting. The central region with a low, constant rate of variant reporting is the region with the least amount of introduced error and therefore the region most suitable for further analysis. The regions at beginning and end of the read which usually have high rates of variant reporting may be excluded from further analysis. In one aspect, this end trimming process may be employed in step (d) to remove the low quality sequence data. In another aspect, the end trimming is based on the bias of variant frequency vs. read position.

In one embodiment, a quality value filtering may be employed in step (d). The sequencing strand coverage may be separated to discriminate sequencing error or to evaluate sequencing quality. For instance, the (+/−) strand coverage may be plotted separately in order to distinguish the "Solexa Base Calling Errors" from the real sequence variants.

In another embodiment, the polynucleotide may be introduced into the plurality of cells by transfection prior to step (a). The polynucleotide may be carried on a plasmid or other vectors. In one aspect, the plasmid carrying the polynucleotide may be sequenced by NGS or by DNA sequencing prior to being introduced into the cells.

Cloning and subcloning are effective ways not only to ensure clonality but also to improve the productivity in some cases. Top transfectants may be subject to single-cell cloning after they have been selected. After single cell-cloning, a second round of screening for the lead candidate clones may be performed. The top selected cells of step (e) may be cultured to produce the protein of interest.

BRIEF DESCRIPTION OF THE DRAWINGS

FIG. 1 illustrates one embodiment of the method by using NGS screening and Mass Spectrometry to assist production cell line development.

FIG. 2 shows evaluation of sequencing quality: variant frequency vs. base position.

FIG. 3 shows application of Q value and end-trimming in sequencing data analysis.

FIG. 4 shows data analysis with more filters applied to reduce background.

FIG. 5 shows sequencing data analysis of CHO line A/A-mut virtual mix.

FIG. 6 shows sequencing data analysis of CHO line A/A-mut virtual mix.

FIG. 7 shows detection of clustered heavy chain (HC) sequence variants in CHO line A/A-mut virtual mix.

FIG. 8 shows RNAseq analysis of CHO line B light chain (LC) and heavy chain (HC).

FIG. 9 shows resequencing of light chain (LC) RT-PCR product derived from CHO line B.

FIG. 10 shows DNAseq analysis of the plasmid used for generating of the CHO line B.

FIG. 11 shows DNAseq analysis of CHO vector for generating of CHO line C.

FIG. 12 shows RNAseq analysis of transfection pool #4 for CHO line C.

FIG. 13 shows Mass Spectrometry confirmation of the heavy chain mutation of pool #4.

FIG. 14 shows RNAseq analysis of a subclone of CHO line C.

FIG. 15 is a diagram showing the process of transfection, amplification and cloning of the CHO cells.

DETAILED DESCRIPTION

Figure 16:
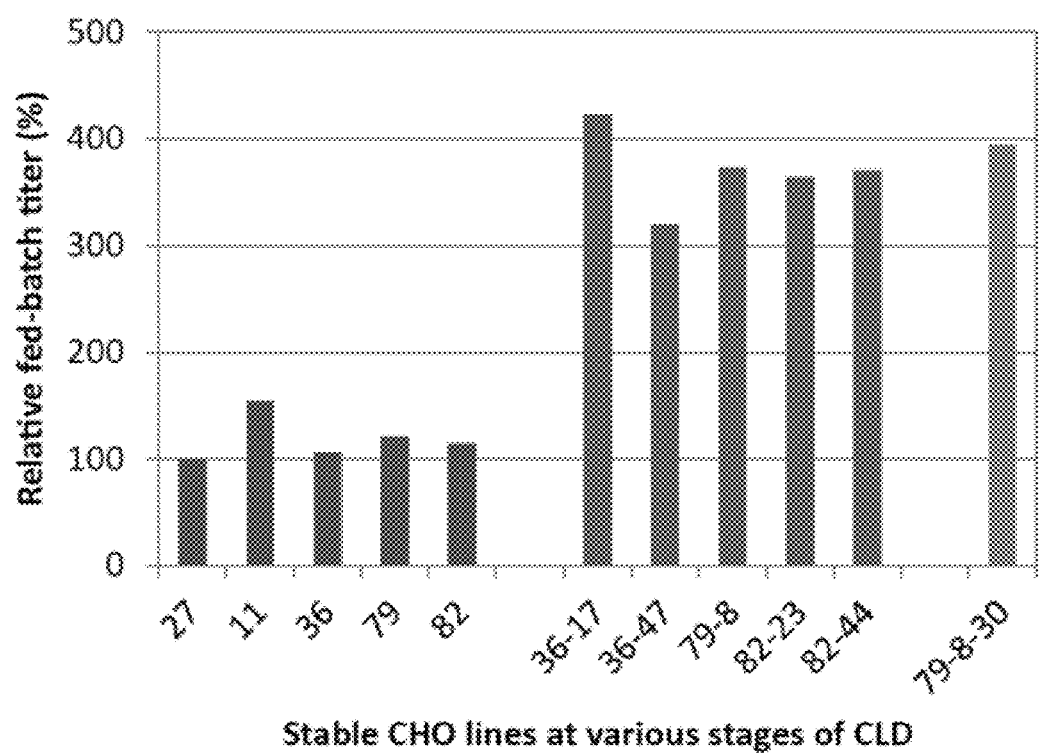
FIG. 16 shows the titer of several top lines during various stages of CLD.

It is disclosed here application of next generation sequencing (NGS) technology to characterize biologic-producing stable cell lines to improve the efficiency of cell line development. Monoclonal antibody-producing stable CHO cell lines are used to illustrate the inventions. The details of developing a novel NGS data analysis package are also reported.

In the past ten years or so, a variety of next generation sequencing (NGS) technologies, featuring sequencing of multi-million templates simultaneously, have been developed. With this enhanced sequencing capacity, NGS technologies have transformed the field of bioinformatics, as well as basic, applied and clinical research. Major commercially available high throughput NGS technologies include, for example, 454 pyrosequencing, Illumina sequencing, SOLiD sequencing, PACBIO RS, HeliScope sequencing, among others. See e.g., Metzker, 2010. More recently, technologies focusing on quick nimble sequencing applications have emerged and gradually became mainstream as well, such as Ion Torrent and Oxford Nanopore technologies.

With high data throughput and sensitivity, NGS technology is promising to play an important role in screening biologics for heterogeneity and contamination. With help of 454 sequencing, Victoria and colleagues successfully identified mutations, minority variants in several live-attenuated vaccines. See Victoria, et al., 2010. Victoria, et al. have also detected trace amount of avian leukosis virus which derived from chicken embryo fibroblasts during vaccine manufacturing.

Deep sequencing of genome and transcriptome has been widely employed in clinical research to discover diverse mutational and splicing events and in cell culture research to identify gene targets for cell line engineering and bioprocess optimization. However, there are few reports on using next generation sequencing (NGS) to identify aberrant cell lines with low abundance mutation at the genomic/transcriptional level. Here, an optimized method for cell line quality control throughout the different development stages is disclosed which combines NGS identification and mass spectrometry confirmation. One embodiment of such methods is shown in FIG. 1.

In one embodiment, Illumina sequencing technology may be used for molecular characterization of monoclonal antibody-producing stable CHO cell lines to assist production CHO cell line development. The details of developing a novel NGS data analysis package are also disclosed.

Prior to setting up any stable CHO line transfection, the nucleotide sequence of the expression vector may be confirmed by NGS to exclude any trace amount of variant contamination. After stepwise methotrexate (MTX) amplification, the high-producing transfectants from independent pools (usually ranging from 5 to 10 transfectants) may be screened based on the genomic characterization via next generation transcriptome sequencing. As the introduction of MTX may lead to increased mutation rate, this early cell line screening step may help eliminate sequence variant-containing lines.

NGS approach typically has 2-3 days of turnaround time when resources permit, and hence, it can be implemented in cell line development process in real time. In contrast, the turnaround time for mass spectrometry method may be as long as 2-3 weeks if representative material from 2-week fed-batch production is used. Thus, although either NGS or mass spectrometry may be used at the transfectant stage for cell line screening, NGS is preferred because of its rapidity and sensitivity.

Cloning and subcloning are effective ways not only to ensure clonality but also to improve the productivity in some cases. After selected transfectants are single-cell cloned, a second round of screening may be implemented for the leading candidate clones (usually ~5 clones) based on NGS RNAseq and complementary mass spectrometry analysis (e.g. reduced mass or peptide mapping). There is no sacrifice in timeline by implementing mass-spec as fed batch production is usually required for examination of other critical product quality attributes at the clone stage. Confirming the nonexistence of sequence variant via mass-spec facilitates making the final decision regarding which two clones would enter the process development stage.

During process development, media and bioprocessing parameters are optimized for better titer and product quality. It is known that amino acid misincorporation may occur when certain amino acids are depleted in CHO cell process, which generates non-genomic-mutation derived sequence variant. Therefore, a check point at the end of process development stage may be implemented in which high sensitive mass-spec methods (e.g. SITRS) may be used to detect a full spectrum of protein sequence variations. When the master cell bank (MCB) is completed, both NGS and high sensitive mass-spec confirmation may be performed for quality assurance release.

It is disclosed here the use of NGS technology, more specifically, RNAseq, to characterize biologic-producing stable cell lines in order to improve the efficiency of Cell Line Development (CLD). In the past decade, a variety of NGS technologies capable of sequencing millions of templates simultaneously have been developed including 454 pyrosequencing, Illumina sequencing, SOLiD sequencing, PACBIO RS, HeliScope sequencing, Ion Torrent, and Oxford Nanopore, etc. (Maitra et al. 2012; Metzker 2010). With the enhanced sequencing capacity, NGS technologies have transformed the field of bioinformatics as well as basic, applied and clinical research (Horner et al. 2010; Mestan et al. 2011; Rizzo and Buck 2012; Shokralla et al. 2012). In this study, Illumina/Solexa sequencing was chosen based on its massive throughput, multiplexibility, high sensitivity and high fidelity. A custom-developed NGS data filtering and analysis package was used to identify and quantitate point mutations which occurred during cell line generation (Liu et al., manuscript in preparation). A limit of detection as low as ~0.2% was achieved with 95% confidence interval and no prior knowledge of the point mutation or the amino acid substitution was required. Furthermore, RNAseq provided a high level of reproducibility for both technical and biological replicates (Wang et al. 2009).

Instead of whole genome sequencing, RNAseq is used in this disclosure due to its greater depth of sequence coverage across the genes of interest at a relatively compact dataset size (i.e. ~5 Gb). As a result, more efficient data collection, simpler data analysis, improved sensitivity, and reduced cost per sample can be achieved. It potentially provides a nearly real-time identification of mutations which allows a prompt go/no-go decision for the intermediate cell line candidates within the time span of two cell passages. Moreover, RNAseq not only detects mutations, deletions or insertions de novo, but also provides valuable information on post-transcriptional modifications such as cryptic splicing. In addition, RNAseq avoids false-positive detection which may occur during whole genome sequencing, for example, when a mutated gene copy is not actively transcribed due to either gene silencing or gene rearrangement/fragmentation. Finally, RNAseq is consistent with the ICH Q5B guidance document that "examination of the transcription product itself by analysis of mRNA or cDNA may be more appropriate than analysis of genomic DNA."

The deduction of a Ser to Leu substitution in heavy chain based on RNAseq result was confirmed via mass measurement of the reduced mAb molecule and peptide mapping with tandem mass spectrometry. A similar approach to identify a sequence variant by RPLC-MS and to characterize it by LC/MS/MS was reported by Fu et al. (Fu et al. 2012). Highly sensitive instrumentation may also be used such as advanced automatic data search packages such as Mascot-ETS, SEQUEST or SIEVE (Yang et al. 2010; Zeck et al. 2012). Other approaches may include stable isotope-tagged reference standard (SITRS) that is capable to identify and quantify low-level amino acid misincorporation by comparing the minute difference between desired product and potential sequence variant (Manuilov et al. 2011). One of the biggest advantages of mass spec-based approach lies in its capability of detecting non-genetic mutation derived sequence variants resulting from either tRNA mischarging or codon misreading (Guo et al. 2010; Khetan et al. 2010; Wen et al. 2009; Yu et al. 2009). However, it is worth noting that the root cause of a given sequence variant cannot be determined only by mass-spectrometer or any other amino acid based analytical approaches unless the corresponding nucleotide sequence is assessed simultaneously (Ren et al. 2011; Zeck et al. 2012; Zhang et al. 2012).

Here an optimized approach is disclosed for cell line quality control on sequence variant throughout the different developmental stages that combines NGS identification and mass spectrometry confirmation (FIG. 1). Prior to setting up any stable CHO line transfection, the nucleotide sequence of the expression vector is confirmed by NGS or DNAseq to exclude the likelihood of plasmid contamination. After stepwise amplification with selecting reagent such as MTX, the high-producing transfectants from independent pools are screened based on the genetic characterization via NGS, or more specifically, RNAseq. Mass spectrometry may be used at this stage for sequence variant screening but RNAseq is preferred because of its high sensitivity and fast turnaround time of 5-7 days in contrast to 2-3 weeks of mass-spec (if representative material from fed-batch production is used). Cloning and subcloning are effective ways not only to ensure clonality/stability but also to improve the productivity in some cases. After selected transfectants are single cell cloned, a second round screening is implemented for the leading candidate clones based on NGS (or more specifically, RNAseq) and complementary mass spectrometry analysis (e.g. reduced mass and peptide mapping). In this step, any genetic variation detected through RNAseq would guide the search for the corresponding amino acid substitution and mass change. There is no sacrifice in timeline by implementing mass-spec as fed batch production is usually required for examination of other critical product quality attributes at the clone stage. Confirming the absence of sequence variants via mass-spec facilitates making the final decision regarding which clone(s) would enter the process development stage. During process development, media and bioprocessing parameters are optimized for better titer and product quality. It is known that amino acid misincorporation may occur when certain amino acids are depleted in CHO cell process, which generates non-genetic-mutation derived sequence variant. Therefore, a check point by the end of process development stage is implemented in which highly sensitive mass-spec methods are used to detect a full spectrum of protein sequence variations. When the master cell bank (MCB) is completed, both NGS (or more specifically RNAseq) and highly sensitive mass-spec confirmation may be performed once again for quality assurance release. It needs to be pointed out that this cell line screening "funnel" is not an isolated practice but rather integrated with other existing quantity/quality-based screening procedures to further improve the efficiency of biotherapeutics development process.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

Generally, nomenclatures used in connection with cell and tissue culture, molecular biology, immunology, microbiology, genetics and protein and nucleic acid chemistry and hybridization described herein are those well known and commonly used in the art. The routine methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The term "Next Generation Sequencing" (NGS) refers to a relatively new sequencing technique as compared to the traditional Sanger sequencing technique. For review, see Shendure et al., Nature Biotech., 26(10): 1135-45 (2008), which is hereby incorporated by reference into this disclosure. For purpose of this disclosure, NGS may include cyclic array sequencing, microelectrophoretic sequencing, sequencing by hybridization, among others. By way of example, in a typical NGS using cyclic-array methods, genomic DNA or cDNA library is first prepared, and common adaptors may then be ligated to the fragmented genomic DNA or cDNA. Different protocols may be used to generate jumping libraries of mate-paired tags with controllable distance distribution. An array of millions of spatially immobilised PCR colonies or "polonies" is generated with each polonies consisting of many copies of a single shotgun library fragment. Because the polonies are tethered to a planar array, a single microliter-scale reagent volume can be applied to manipulate the array features in parallel, for example, for primer hybridization or for enzymatic extension reactions. Imaging-based detection of fluorescent labels incorporated with each extension may be used to acquire sequencing data on all features in parallel. Successive iterations of enzymatic interrogation and imaging may also be used to build up a contiguous sequencing read for each array feature.

"RNAseq" refers to RNA Sequencing, or more specifically, total transcriptome sequencing, i.e., the sequencing of all messenger RNA in a sample.

The term "transcriptome" refers to the set of all RNA molecules, including mRNA, rRNA, tRNA, and other non-coding RNA produced in a cell or in a population of cells.

The term "Read" is used to refer to NGS data or DNA sequence, obtained from one molecule of the sample. The complete data set is a collection of reads obtained from a sample.

"RefSeq" means Reference sequence, and refers to nucleotide sequence of interest, such as a plasmid or messenger RNA sequence.

The term "polynucleotide" comprises DNA or RNA molecules.

The term "variant" refers to a mismatch (disagreement) between a nucleotide (or amino acid) of the data and the corresponding nucleotide (or amino acid) in the reference sequence. The difference in amino acid sequence may be caused by the addition (e.g., insertion), deletion, or conservative substitution of amino acids. A conservative substitution of an amino acid, i.e., replacing an amino acid with a different amino acid of similar properties (e.g., hydrophobicity and degree and distribution of charged regions) is recognized in the art as typically involving a minor change. These minor changes can be identified, in part, by considering the hydropathic index of amino acids, as understood in the art (see, e.g., Kyte et al. (1982) J. Mol. Biol. 157: 105-132). The hydropathic index of an amino acid is based on a consideration of its hydrophobicity and charge. It is known in the art that amino acids of similar hydropathic indexes in a protein can be substituted and the protein still retains protein function. In one aspect, amino acids having hydropathic indexes of ±2 are substituted. The hydrophobicity of amino acids also can be used to reveal substitutions that would result in proteins retaining biological function. A consideration of the hydrophobicity of amino acids in the context of a peptide permits calculation of the greatest local average hydrophobicity of that peptide, a useful measure that has been reported to correlate well with antigenicity and immunogenicity (see, e.g., U.S. Pat. No. 4,554,101). Substitution of amino acids having similar hydrophobicity values can result in peptides retaining biological activity, for example immunogenicity, as is understood in the art. In one aspect, substitutions are performed with amino acids having hydrophobicity values within ±2 of each other. Both the hydrophobicity index and the hydrophobicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophobicity, charge, size, and other properties. The term "variant" encompasses fragments of a variant unless otherwise defined. A variant may be at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or at least 75% identical to the wild-type sequence.

As used herein, the "percentage of sequence variants" in a cell refers to a cell containing a heterogeneous population of polynucleotides, wherein at a given position of the polynucleotides, at least one variant exists which has a different nucleotide at the position that is different from that of the reference sequence. The ratio between the total populations of these variants and the total polynucleotides expressed as a percentage is the percentage of sequence variants. In theory, the percentage of sequence variants may range from 0-100%, but for purpose of selecting a production cell line for production of a protein, it is desirable to distinguish a cell line having as little as 2%, 1%, 0.5%, or even 0.1% sequence variants. One limitation of traditional sequencing is limited sensitivity in detecting low percent sequence variants. By using NGS alone or in combination of MS methods, the methodology disclosed herein is capable of detecting less than 2%, less than 1%, or even lower sequence variants.

Q Score is the abbreviation of Quality score, and is a numerical assignment by the instrument software of the overall quality of a basecall.

NQS stands for Neighborhood Quality Score and is the average score of the bases included in a window centered on the nucleotide being analyzed. An NQS of 20 for a window of 5 means the quality score average for the nucleotide being analyzed and two nucleotides before and two after is 20.

The term "End Trim" means exclusion of data from the ends of reads due to low sequencing quality.

The term "Mapping" refers to the process of matching the read data to a position in the reference sequence. The matching may be imperfect due to the presence of variants.

The term "antibody" refers to an immunoglobulin (Ig) molecule, which is generally comprised of four polypeptide chains, two heavy (H) chains and two light (L) chains, or a functional fragment, mutant, variant, or derivative thereof, that retains the epitope binding features of an Ig molecule. Such fragment, mutant, variant, or derivative antibody formats are known in the art. In an embodiment of a full-length antibody, each heavy chain is comprised of a heavy chain variable region (VH) and a heavy chain constant region (CH). The heavy chain variable region (domain) is also designated as VDH in this disclosure. The CH is comprised of three domains, CH1, CH2 and CH3. Each light chain is comprised of a light chain variable region (VL) and a light chain constant region (CL). The CL is comprised of a single CL domain. The light chain variable region (domain) is also designated as VDL in this disclosure. The VH and VL can be further subdivided into regions of hypervariability, termed complementarity determining regions (CDRs), interspersed with regions that are more conserved, termed framework regions (FRs). Generally, each VH and VL is composed of three CDRs and four FRs, arranged from amino-terminus to carboxy-terminus in the following order: FR1, CDR1, FR2, CDR2, FR3, CDR3, and FR4. Immunoglobulin molecules can be of any type (e.g., IgG, IgE, IgM, IgD, IgA and IgY), class (e.g., IgG1, IgG2, IgG3, IgG4, IgA1 and IgA2), or subclass.

The term "biological function" refers the specific in vitro or in vivo actions of a binding protein. Binding proteins may target several classes of antigens/ligands and achieve desired therapeutic outcomes through multiple mechanisms of action. Binding proteins may target soluble proteins, cell surface antigens, as well as extracellular protein deposits. Binding proteins may agonize, antagonize, or neutralize the activity of their targets. Binding proteins may assist in the clearance of the targets to which they bind, or may result in cytotoxicity when bound to cells. Portions of two or more antibodies may be incorporated into a multivalent format to achieve distinct functions in a single binding protein molecule. The in vitro assays and in vivo models used to assess biological function are known to one skilled in the art (US 20090311253).

Binding proteins may be produced using a variety of host cells or may be produced in vitro, and the relative yield per effort determines the "production efficiency." Factors influencing production efficiency include, but are not limited to, host cell type (prokaryotic or eukaryotic), choice of expression vector, choice of nucleotide sequence, and methods employed. The materials and methods used in binding protein production, as well as the measurement of production efficiency, are known to one skilled in the art. See, e.g., U.S. Patent application Publication 20090311253.

The terms "recombinant host cell" or "host cell" refer to a cell into which exogenous DNA has been introduced. Such terms refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells. In an embodiment, eukaryotic cells include protist, fungal, plant and animal cells. In another embodiment, host cells include but are not limited to the prokaryotic cell line *E. Coli*; mammalian cell lines CHO, HEK293, COS, NS0, SP2 and PER.C6; the insect cell line SP9; and the fungal cell *Saccharomyces cerevisiae*.

It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1

Illumina Sequencing

Among the NGS technologies, 454 pyrosequencing, Illumina sequencing and SOLiD were evaluated. 454 technology, which generates long reads around 400 bp, is ideal for genomic scaffold building and defining gene linkage information. However the 454 technology performs less accurately around homopolymer regions. SOLiD boasts a 2-color base-calling algorithm. However, the SOLiD RNAseq methodology produces strand specific read datasets that are incompatible with the analysis developed here in this embodiment. The analysis of this embodiment requires comparison and agreement of data from both strands. Illumina sequencing has been NGS market dominator for many years. The Illumina HighSeq 2000 system generates high quality data with massive throughput at ~300 Gb/run. Illumina sequencing was used in the test system here for characterization of biologic-producing stable CHO lines.

Preparation of sequencing templates for RNAseq-Five million CHO cells were collected from specific cell line development stages, rinsed with PBS once. Total RNA of CHO samples was prepared by using TRIZOL reagent according to the instruction provided by the manufacturer (Life Technology, Carlsbad, Calif., USA). Poly(A) mRNA was purified by oligo(dT) beads (Life Technology, Carlsbad, Calif., USA).

RNAseq sequencing library preparation and Illumina sequencing—The purified mRNA samples were fragmented to 200 bp-500 bp and reverse-transcribed using random hexamers. Short cDNA fragments were purified with QiaQuick PCR extraction kit (Qiagene, Hilden, Germany) and followed by end repair and poly (A) addition. Sequencing adaptors were then added to the ends of the 3' A-tailed cDNA fragments. After size selection and PCR amplification of the sequencing fragment libraries, 51 bp or 91 bp pair-end reads were generated using an Illumina HiSeq 2000 (Illumina, San Diego, Calif., USA).

DNAseq sequencing library preparation and Illumina sequencing-DNAseq (resequencing) of plasmid vector was applied to characterize a CHO vector used for stable CHO line generation. The plasmid DNA stock was sequenced using Illumina SBS chemistry on a MiSeq instrument (Illumina, San Diego, Calif., USA). A sequencing library was prepared from 1 ng of plasmid using the Nextera XT DNA Sample Preparation Kit (Cat. #: FC-131-1024. Illumina, San Diego, Calif., USA) with dual indexes (barcodes). The manufacturer's protocol was followed, including the library normalization step. The sample was sequenced as a paired end library using 2×250 base reads with version 2 chemistry. A total of 4.1 million reads were obtained and analyzed.

Example 2

NGS Data Analysis

Data mapping to reference file by Bowtie-Mapping of read data to reference sequences was performed by the open source program Bowtie 0.12.5. The mapping parameters were chosen to allow significant mismatch between data and RefSeq. This permitted reporting of reads with multiple mismatches. The typical command line for mapping reads 50 nucleotides long was: Bowtie -t -n 3 -1 15 -e 200 <index> <data file name> <output file name>, where each term used was define in table 1:

TABLE 1

| | Explanation of terms used in Bowtie mapping. |
|---|---|
| -t | track wall clock time for the process. |
| -n 3 | allow 3 mismatches in the 'seed' region. The default is 1. |
| -1 15 | use a 'seed' region 15 nucleotides long. The default is 28. |
| -e 200 | allow the sum of the mismatches' quality scores to equal 200 before rejection. The default is 70. |
| <index> | the index file prefix. RefSeqs were processed into a table of index 'keys' used to find the match 'seeds'. The process of indexing speeds the mapping process for large RefSeqs such as genomes. |

The mapping output file had the Bowtie default 8 column output as described in the documentation. The Bowtie output file was the input data for both the tally of variants by read position and tally of variants by position in RefSeq.

Tally of variants by position in read—The second step of analysis was to tabulate the variants reported by Bowtie by their position in the read. The tally was performed by a custom script and includes totals of all mismatches by nucleotide, totals of quality scores by nucleotide for each position of the read and total reads processed. In order to be included in the tabulation, a mismatch must meet the minimum base quality score and a minimum NQS. The minimum base quality score was set to 10-20. The minimum NQS was set to 20 and the NQS window was 3-11. The NQS was built-in in future data analysis process as default unless otherwise specified. Data is expressed as variants per million reads per position in the read. Each nucleotide (A, C, G, T) was tallied separately as are the quality scores of the variant bases. Aggregate quality for the reported variants is also calculated. Results were written to a tab-delimited text file which was imported into an Excel workbook and plotted for each nucleotide individually as variants/million reads (Y-axis) vs. read position (X-axis). The read position was identical to the sequencing cycle number.

End trimming of read data-Similar to traditional Sanger sequencing, the quality of each base on a short read varies. Schroder J et al. (2010) analyzed the base frequency at each base position of Illumina short reads, and found that the 5-8 bp data at 5' end was of low quality. It is to be recognized that factors such as sequencer status, end repair during library preparation and adaptor addition may all potentially impact data quality during the beginning sequencing cycles.

A novel data filtering process was developed to determine data quality at each position by investigating mismatch/variant frequency at each by locations of the short reads. For a high quality data set, the plot typically shows an abundance of mismatches at both ends of the read and a central region with a low and constant rate of variant reporting. The central region with a low, constant rate of variant reporting was the region with the least amount of introduced error and therefore the region most suitable for further analysis. The regions at beginning and end of the read which had (abnormally) high rates of variant reporting were excluded from further analysis (FIG. 2). The data that remained after end trimming was the "usable range" of the read.

Tally of Variants by Match Position in RefSeq—The fourth step of analysis was to tally the mapping data of step One above by position in the RefSeq using a custom script. The tally was limited to the 'usable range' of the reads as determined in step Three above. Minimum quality score was set at 10-20 for individual base calls and 20 for the NQS using a window of 3-11. The NQS was built-in in the future data analysis process as default unless otherwise specified. Separate tallies were kept for the (+) and (-) strands. Total reads on each strand at each position of the reference sequence were also tallied. The tally was written to a tab-delimited text file which was imported to an Excel workbook for additional calculation and display.

Analysis of the RefSeq Variant Tally—The tallied data was used to calculate the variance at each position of the RefSeq, mean variance and standard deviation for regions of interest, e.g. open reading frames. The variance was the number of mismatches expressed as percent of total reads covering the position. The mean was the average variance for a region and the standard deviation was calculated for the same region. Plus and minus strand results were calculated separately.

For each position of the RefSeq, the information items determined were described in Table 2 below.

TABLE 2

Information items collected during data analysis.

| | |
|---|---|
| Variant | mismatches as a percent of the total reads covering the position |
| Basecall | the majority variant for each strand at the position |
| Pass same basecall | if both (+) and (−) strands report the same majority variant |
| Pass minimum threshold | if both (+) and (−) strand variance meets minimum threshold |

For each region of interest, e.g. open reading frame or complete transcript, the following were determined: mean, namely average variance for the region, and standard deviation for the region. The mean and standard deviation for a region of interest were used to determine whether positions that had variance were of sufficient magnitude to report. The minimum threshold filter was typically set to the mean plus two standard deviations.

FIG. 4 shows a typical data filtering for a heavy chain (HC) data set of a CHO line sample. When Q>20 and end trimming filters were applied, the background was within 0.1% range but many peaks were reported. Although the background range did not decrease significantly after addition of one more filter: same basecall, the number of variant positions reported was reduced. After addition of the last filter: minimum threshold of mean plus 2 standard deviations, only 1 variant call remains: bp 1805, C>G at 0.37%.

Example 3

Detection of Sequence Variants in a Virtual Mix

CHO Line A and its mutant version Line A-mut were subjected for Illumina sequencing according to the methods described in the previous examples. Both lines shared the same antibody sequences except that Line A-mut carried an L234A, L235A mutant human gamma 1 Fc. On the cDNA level, the HC of line A and A-mut have 6-base differences in the coding region (Table 3). The Line A-mut dataset contained 27.9 million reads, of which 1.02 million (3.66%) could be mapped to its reference sequence. The Line A dataset contained 31.8 million reads, of which 0.41 million (1.29%) could be mapped to its reference sequence (Table 4).

TABLE 3 cDNA sequence difference between CHO line A and A-mut.

| Position (bp) | A-mut | A |
|---|---|---|
| 1281 | C | T |
| 1671 | T | C |
| 2023 | G | C |
| 2024 | C | T |
| 2026 | G | C |
| 2027 | C | T |

TABLE 4

Illumina sequencing result of CHO line A and A-mut.

| | Total Reads (Millions) | Total Matches to Ab reference (Millions) | Match rate |
|---|---|---|---|
| A-mut | 27.9 | 1.02 | 3.66% |
| A | 31.8 | 0.41 | 1.29% |

To validate the data analysis package, reads from A-mut and A datasets were virtually mixed at a ratio of 99 to 1. The virtual mix data set was then subjected to Bowtie mapping, filtering for Q>20 and end trimming to remove the 10 bases at the beginning and the end of each read. The (+) and (−) strand results were kept separate in order to distinguish the "Solexa Base Calling Errors" from the real sequence variants. As shown in FIG. 5, all 6 sequencing variants were accurately detected at around 1%. Two artifacts, at bases 1421 and 1621, were correctly identified by separating strand coverage (FIG. 6). The details of correct detection of the variant cluster at base 2023-2024 and 2026-2027 were shown in FIG. 7.

Example 4

Detection of a Sequence Variant in a CHO Line

During a production campaign, an N158K mutation in antibody light chain (LC) was detected at 1.5% in a CHO line B by SITRS analysis, a sensitivity-enhanced MS method. The stable CHO line sample was subjected to Illumina sequencing according the previous description. The RNAseq data was then analyzed by Bowtie mapping and filtering including Q>20, end trimming to remove the 10 bases at the beginning and the end of each read. The (+/−) strand coverage was plotted separately in order to distinguish the "Solexa Base Calling Errors" from the real sequence variants.

As showed in FIG. 8, a 1.1% mutation, C>G at base 7987, corresponding to N158K, was identified in LC by RNAseq analysis. A "Solexa Base Calling Error" was also detected at bp7577. Analysis of the corresponding HC data revealed no mutation.

Resequencing of LC RT-PCR product also detected the same C>G mutation at the same level at base 7987 (FIG. 9). However, resequencing of the plasmid used for generating of the CHO line B did not show any mutation at by 7987 (FIG. 10), suggesting that the mutation was acquired during CHO line development.

Example 5

NGS Screening in Support of Production CHO Line Development

NGS was used to investigate the mutation-occurring pattern in the whole process of CHO line C development. In addition to data filters such as Q>20 and end trimming, extra filters such as same base call and minimum threshold, were applied in data analysis.

Resequencing of the CHO vector for CHO Line C revealed a 0.26% A>G mutation at base 251 in HC open reading frame (FIG. 11). Considering the low mutation rate, the vector was still used in transfection of CHO cells.

During the development of CHO line C, 11 samples was collected and subjected to NGS sequencing: including 5 stable transfectants, 5 CHO clones and 1 subclone.

Among the 5 stable transfectants, three showed no mutation in either HC or LC. However a 1.64% C>T mutation at base 407 was detected in HC derived from pool #4, resulted in an S117L mutation in amino acid sequence. A 0.43% A>C mutation at bp 132, which resulted in a K24N mutation in amino acid sequence, was also detected in LC (FIG. 12). The HC mutation was further confirmed by diphenyl reverse phase separation of the reduced antibody followed by ESI-QTOF MS analysis, which showed a 3%+26 Dalton HC variant resulting from the Serine to Leucine mutation (FIG. 13). The fifth transfectant had the same HC mutation, but no LC mutation.

None of the 5 CHO clones sequenced showed any mutation in either HC or LC (Data not shown).

As shown here, mutations, especially low-abundance mutations could occur at any stage during cell line development. Some mutations may occur naturally during regular DNA synthesis, with an estimated rate of 1 in $10^9$. See, McCulloch S D & Kunkel T A, Cell Research 2008; 18: 148-161. Others may result from physical stress and chemical induction during cell line development.

Electroporation is a popular method used in CHO cell transfection. Electroporation type pulsed electric field not only produces transient or permanent permeabilization of cell membrane, but may also cause DNA damage in aqueous solution. See, Golberg A & Rubinsky B. Technology in Cancer Research and Treatment 2010; 9: 423-430. Methotrexate (MTX)-induced gene amplification through dihydrofolate reductase (DHFR) is commonly applied to improve the expression level of stable CHO lines. It was reported that MTX may induce misincorporation of uracil into DNA (Goulain M, et al. Proc. Natl. Acad. Sci. 1980; 77:1956-1960) and oxidative DNA damage (Martin S A, et al. EMBO Molecular Medicine 2009; 1: 323-337). Given the relatively frequent mutation rate during cell line development, applying sensitive mutation-screening methods, such as NGS, may help efficiently exclude mutant lines and speed up the cell line selection process.

Example 6

Use of Sequencing to Select High Producing Cell Lines with Low or No Variants

In order to select the cell line with the highest productivity, 6 µM MTX was used to amplify the transfectants carrying the expression vectors. Five top producers (11, 27, 36, 79 and 82) that had been derived from three independent transfection pools, were selected for further fed-batch evaluation (FIG. 15). A subsequent cloning step was taken on presumably heterogeneous transfectants 36, 79 and 82. Five clones including 36-17, 36-47, 79-8, 82-23 and 82-44 outcompeted the other clones and exhibited 2-3 fold increases in fed-batch productivity compared to the parental transfectants (FIGS. 15 and 16). It is noted that the longer duration of fed batch production due to the temperature shift at day 5 for all clones may also contribute to the significantly elevated productivity, in addition to the cloning effect. In an effort to further improve the productivity, clone 79-8 was chosen to enter a second round of cloning (i.e. subcloning). However, the most productive subclone 79-8-30, despite its improved specific productivity (Qp) (data not shown), showed no further enhancement in fed-batch titer compared to the parental clone 79-8 (FIGS. 15 and 16).

Detailed procedures for cell line generation and amplification are described below. A DHFR-deficient CHO parental cell line adapted to suspension culture in a proprietary serum-free, chemically defined medium was transfected with an expression vector containing the IgG1 mAb light chain (LC) and heavy chain (HC) sequences. Multiple independent transfections were set up and three pools that survived two-step MTX treatment from 100 nM to 500 nM were dispensed in 96-well plates via limiting dilution. After 2-3 week incubation, supernatant samples from growth-positive wells that gave at least 50% confluence were submitted for IgG ELISA screening. Only top producers at this stage were selected for cell culture expansion in larger cell culture vessels (e.g. 12-well plate and T flask) and simultaneously entered another round of MTX amplification up to 6 µM. Based on the batch titer measured by Octet (Pall ForteBio, Menlo Park, Calif.), only top-ranked transfectants were further adapted in suspension, banked and subsequently evaluated in a fed-batch production experiment. To ensure the clonality/expression stability, these fully-amplified, high-producing transfectants were single-cell cloned at a density of 30 viable cells per 96-well plate. All clones were then ranked based on their productivity in multiple-well plates and the top few entered the final fed-batch evaluation in shake flask prior to the process development and optimization. Throughout the entire cell line development process, all cell cultures were incubated at 36° C., 5% $CO_2$ and about 95% humidity. For suspension culture in shake flasks, cells were agitated at 140 rpm in a MultiTronII ATR incubator (Appropriate Technical Resources, Laurel, Md.). Cell viability and viable cell density (VCD) were determined using a ViCell (Beckman Coulter, Fullerton, Calif.).

Detailed procedures for fed batch production are described below. Cells were seeded at 0.5 million viable cells/mL into proprietary chemically defined production media to initiate the fed batch production process. A total volume of 50 mL culture in 250 mL Erlenmeyer disposable non-baffled shake flasks were agitated at ~140 rpm in a MultiTronII ATR incubator at 35° C., 5% CO2 and 95% humidity. Proprietary feed medium was fed on day 3, 5, 7, 9 and 11 at 3, 5, 7, 10 and 10% of initial working volume respectively. Fed-batch cultures were terminated when viability dropped below 50%. The level of glucose and lactate were closely monitored daily by automated Poly-Chem (Polymedco, Cortlandt Manor, N.Y.) and additional glucose feed was only given to the cell culture as needed. Fed-batch cultures were sampled every other day to check cell viability and VCD. The mAb titer was measured by Poly-Chem and was confirmed by Poros A assay. For the final round fed-batch evaluation of clones and subclones, temperature shift to 31° C. was applied on day 5.

Figure 17:
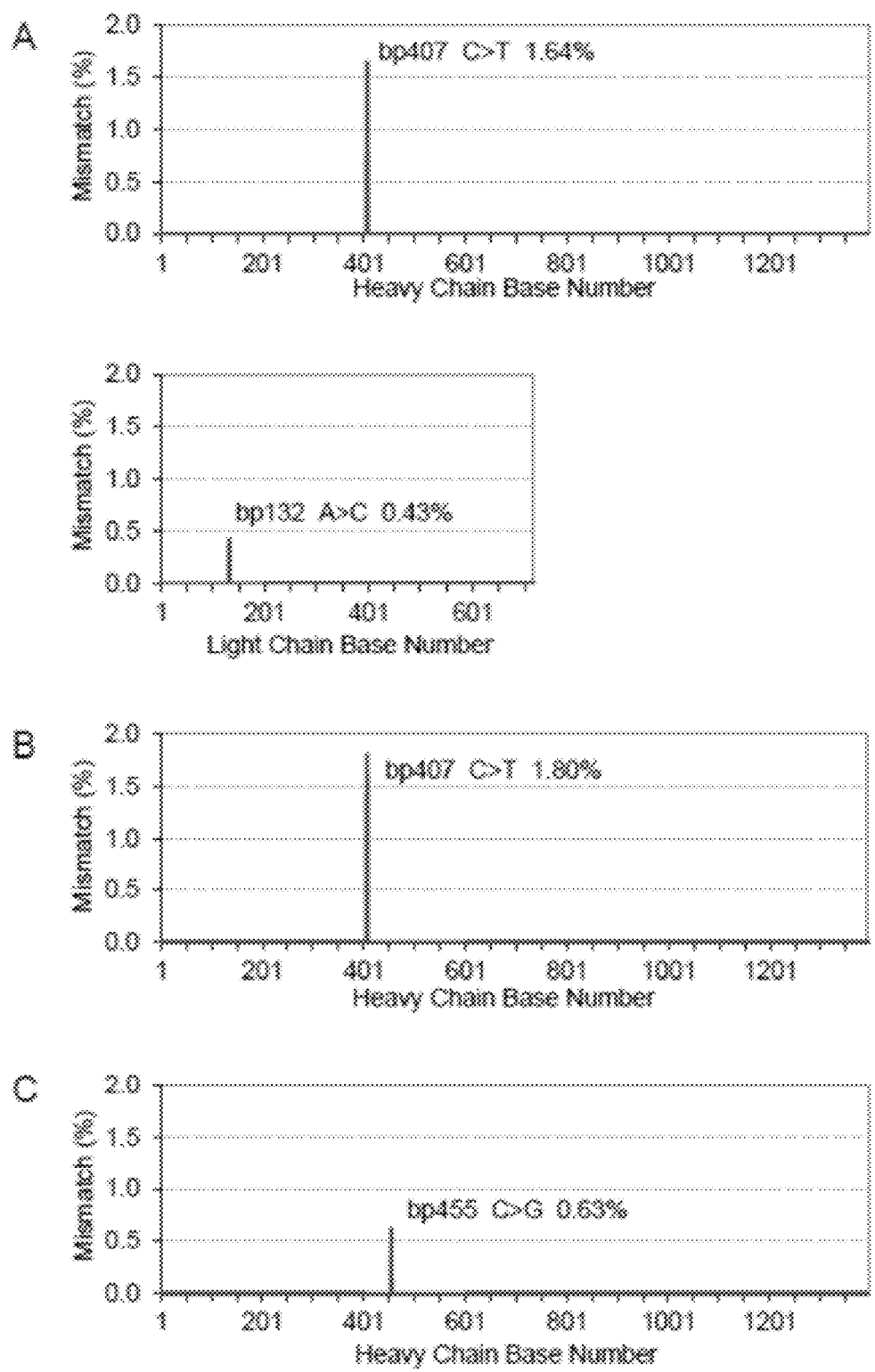
FIG. 17 shows RNAseq analysis of Transfectant 27 (A), Transfectant 11 (B), and subclone 79-8-30 (C).

During the development of stable CHO cell lines expressing the mAb IgG1, samples from 11 cell lines were collected and subjected to RNAseq including 5 transfectants, 5 clones and 1 subclone as shown in FIG. 15. For each of the 11 samples sequenced, the dataset contained 30-35 million paired end reads. Under the permissive matching conditions used, 2-7% of the raw reads mapped to heavy and light chain coding sequences. This gives a range of average read depths of 40,000-100,000 per position. Data quality also varies from sample to sample resulting in a range of cutoff values between 0.06-0.2%. Among the five transfectants, 36, 79 and 82 exhibited no mutation in either heavy chain or light chain coding sequence at a 0.2% threshold of detection (data not shown). For transfectant 27, a C/T mutation (1.64%) at 407 base pair (bp) of the HC coding sequence was detected, suggesting a Ser (TCA) to Leu (TTA) change at residue 117 in HC. Transfectant 11 contained the same C/T mutation (1.8%) at 407 bp and also an A/C mutation (0.43%) at 132 bp of the LC coding sequence which corresponds to a Lys (AAA) to Asn (AAC) substitution at residue 24 in LC (FIGS. 17A and 17B).

Consequently, transfectants 11 and 27 were excluded from further cell line development despite having titers comparable to other leading transfectants. RNAseq was also performed on 5 top-ranked clones including 36-17, 36-47, 79-8, 82-23 and 82-44. None of them contained any mutation in either HC or LC coding sequence, seemingly because these clones were derived from mutation-free, parental transfectants. In spite of the clean background of its parental clone, 79-8, subclone 79-8-30 contained a C/G mutation (0.63%) at 455 bp in the HC coding sequence which corresponds to a Ser (TCA) to Stop (TGA) at residue 133 in HC (FIG. 17C).

Details of CHO cell RNAseq are described below. For each cell line tested, five million viable cells from regular cell culture passage were collected. Total RNA was extracted using TRIZOL reagent according to the instruction provided by the manufacturer and poly(A) mRNA was subsequently purified by oligo(dT) beads (Life Technology, Carlsbad, Calif.). In the next step, mRNA was fragmented to 200-500 base pairs and reverse-transcribed using random hexamer primers. Short cDNA fragments were purified with the QiaQuick PCR extraction kit (Qiagene, Hilden, Germany) and followed by end repair and A-tailing. Sequencing adaptors were then ligated to the ends of the 3' A-tailed cDNA fragments. After size selection and PCR amplification of the sequencing fragment libraries, 91-base paired end reads were generated using an Illumina HiSeq 2000 (Illumina, San Diego, Calif.).

More details of NGS data analysis are described below. The open source program Bowtie0.12.5 was used to map read data to the heavy and light chain reference sequences (Langmead et al. 2009). Mapping parameters were set to allow significant mismatch between data and the reference sequence including: allowing maximum mismatch in the seed region (n=3), reduced seed length (l=15) and increased upper limit on mismatch quality score sum (e=200). Only the forward read was used for mapping to reference sequences. Data from the ends of reads, typically 10% of the 5'-end and 20% of the 3'-end, were excluded from further analysis due to abnormally high rates of mismatch reported. After minimum quality score filtering (Q>=20), the mapping data and mismatches reported were tallied by position in the reference sequence using a custom script (Liu et al., manuscript in preparation). Plus and minus strands were tallied separately. The average number of mismatches per position and standard deviation were calculated and a minimum threshold for reporting was set to the mean plus two standard deviations in order to reflect individual sample data quality. Sequence variants were required to pass minimum threshold and to report the same base change on both strands.

Plasmid deep sequencing (DNAseq) was performed as described below. The expression vector used for the stable CHO line generation was sequenced using Illumina SBS chemistry on a MiSeq instrument (Illumina, San Diego, Calif.). Briefly, a sequencing library was prepared from 1 ng of plasmid using the Nextera XT DNA sample preparation kit with dual indexes following the manufacturer's protocol (Illumina, San Diego, Calif.). The sample was then sequenced as 2×250-base paired end reads which were mapped to the plasmid reference sequence and analyzed as described for RNAseq.

Figure 18:
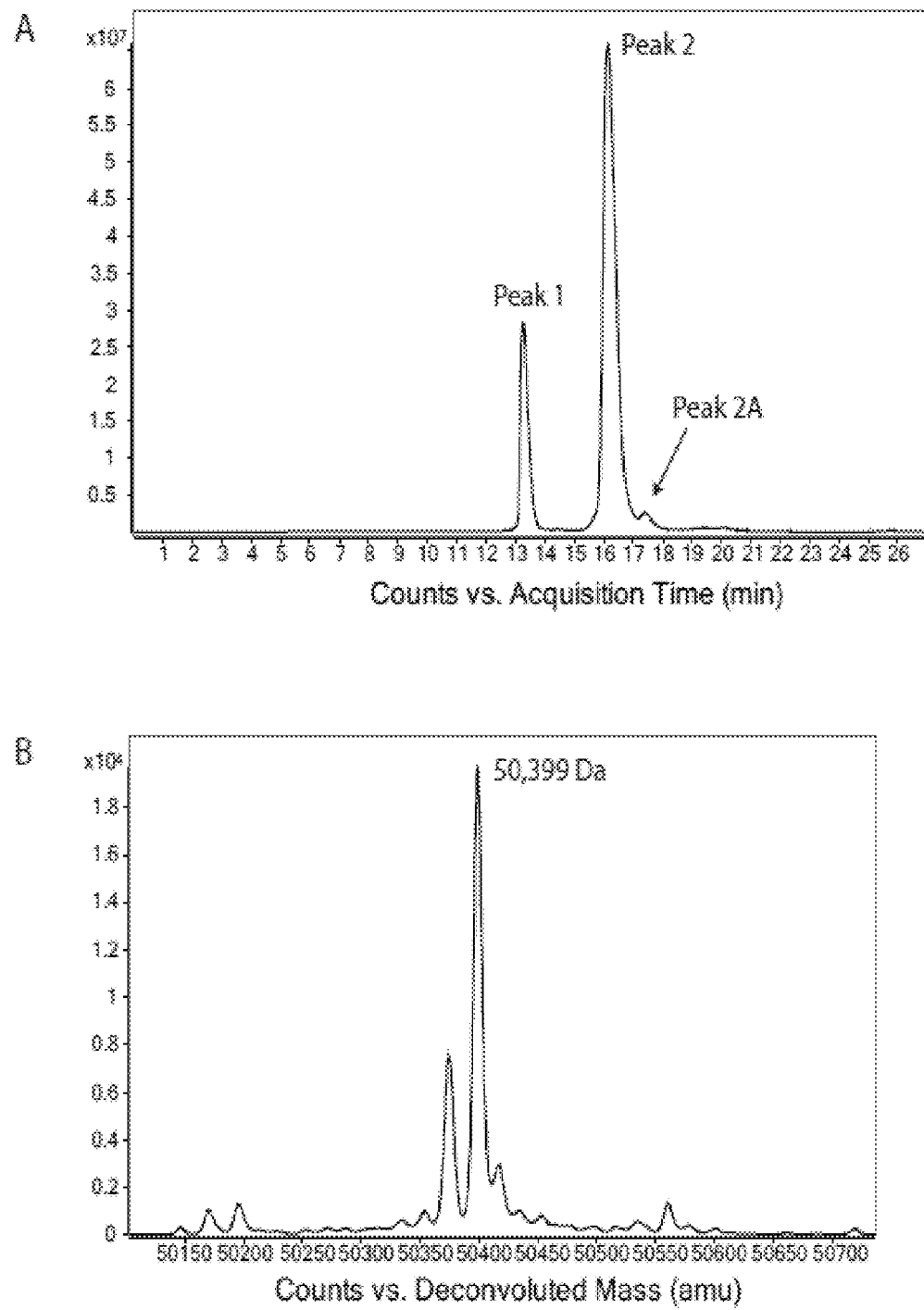
FIG. 18 shows result of reverse phase liquid chromatography confirming the mutations in Transfectant 27 and 11.

In order to confirm the RNAseq results that indicated a low-level Ser117Leu substitution in transfectants 11 and 27, mAb produced by transfectant 11 was reduced into LC and HC subunits and subsequently separated via reverse phase liquid chromatography with ESI-QTOF detection. Besides two main peaks 1 and 2, eluted at 13.2 min and 16.2 min, a shoulder peak in proximity to peak 2, peak 2A, was also observed (eluted at 17.4 min) (FIG. 18A). The deconvoluted mass spectra for all three peaks were collected using an ESI-QTOF mass spectrometer and the predominant observed masses were verified against the theoretical masses of LC and HC (23,815 Da and 50,373 Da respectively). The predominant masses identified for peak 1 and 2 are in agreement with the theoretical values of LC and HC respectively (data not shown). The predominant mass of the peak 2A observed is approximately 26 Da greater than the theoretical HC mass, which is consistent with the mass change expected from a Ser to Leu (FIG. 18B). This additional shoulder peak and the corresponding mass increase of 26 Da were also observed in transfectant 27 but not in other cell lines on which RNAseq was performed (data not shown). The relative area percentage of the HC variant to the total HC calculated based on the total ion chromatogram (TIC) was 3.4% for transfectant 11 and 3.1% for transfectant 27, which are in line with the quantification of C/T point mutation through RNAseq.

Reduced LC/MS analysis was performed as described below. Protein A purified mAb samples from fed-batch harvest were diluted to 1 mg/mL and reduced with the addition of 100 mM dithiothreitol (DTT) followed by incubation at 37° C. for 30 min. The reaction was quenched by lowering pH with trifluoroacetic acid (TFA). Samples were analyzed on an Agilent ESI-QTOF model 6510 mass spectrometer coupled to an Agilent 1200 capillary HPLC system (Agilent Technologies, Santa Clara, Calif.). The reduced samples were separated into the LC and HC subunits for introduction into the mass spectrometer using an Agilent reverse phase diphenyl 1.0 mm×150 mm, 3 μm column. A binary gradient with 0.02% TFA, 0.08% formic acid in water as mobile phase A (MPA) and 0.02% TFA, 0.08% formic acid in acetonitrile as mobile phase B (MPB) was applied at a flow rate of 50 μL/min. The mass spectrometer was run in positive ion mode with a capillary voltage of 4750 V, drying gas temperature of 350° C., fragmentor of 350 V and skimmer of 100 V.

Figure 19:
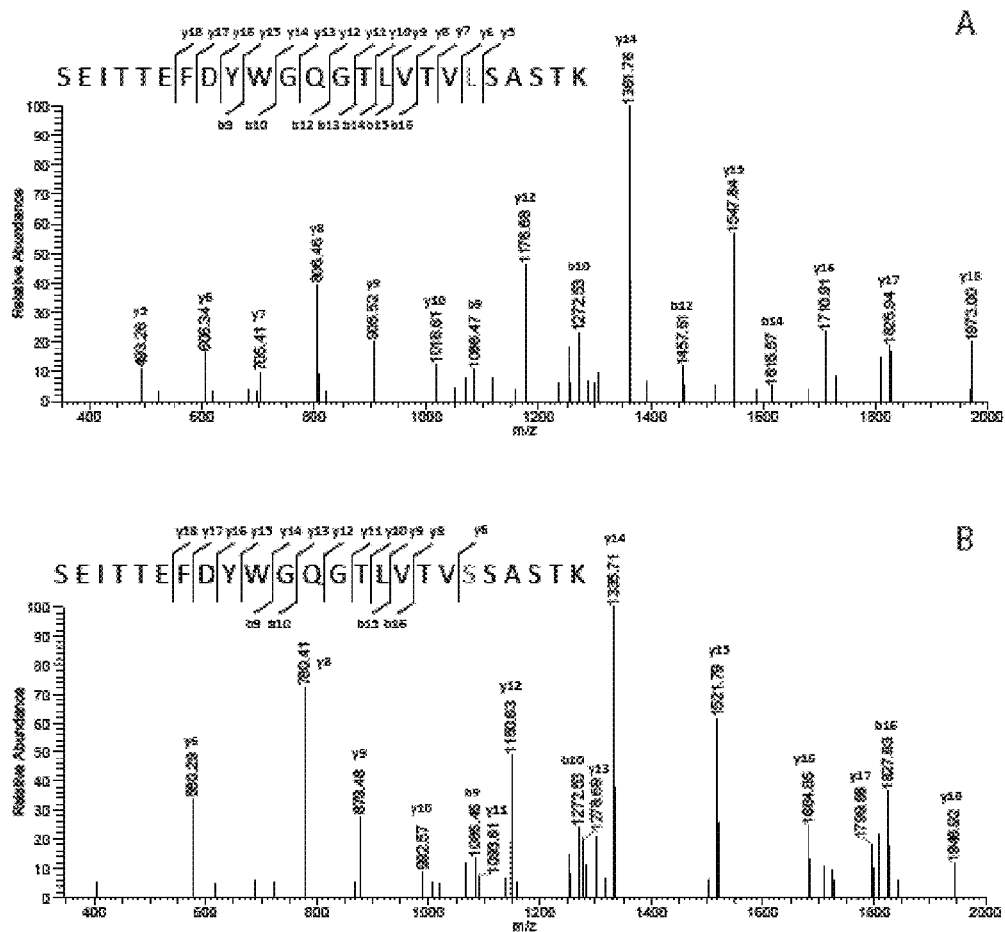
FIG. 19 shows result of Mass Spectrometry confirming that the +26 Da shoulder peak observed in transfectants 11 and 27 bp reduced LC/MS results from a Ser (Panel B, SEQ ID No. 2) to Leu (Panel A, SEQ ID No. 1) substitution at HC-Ser117.

To confirm that the +26 Da shoulder peak observed in transfectants 11 and 27 bp reduced LC/MS results from a Ser to Leu substitution at HC-Ser117, mAb produced by transfectants 11 and 27 as well as mutation-free cell lines including transfectant 36, clones 36-17 and 36-47, were digested with trypsin and analyzed by reverse phase HPLC-MS. The native tryptic peptide containing the Ser117 (HC99-122) has a theoretical molecular weight (MW) of 2606.24 Da while the MW of mutant tryptic peptide HC99-122-Leu117 is 2632.29 Da. The masses of the corresponding +2 and +3 m/z charge states of the Leu117 variant (1317.15 and 878.44 respectively) were only identified in transfectants 11 and 27 and were not observed in transfectant 36 or clones 36-17 and 36-47. The MS/MS spectrum of the +2 m/z charge state of the HC99-122-Leu117 variant (SEQ ID NO.1) was compared to the native HC99-122-Ser117 (SEQ ID NO.2) in FIG. 19. Analysis of the MS/MS spectrum of the variant shows no mass shift in the y5 ion and a mass increase of +26 Da in the y6 to y18 ions, indicating an amino acid change from Ser to Leu at residue 117 of the native peptide as is predicted from the C/T mutation at 407 bp via RNAseq.

Tryptic digestion and peptide mapping were performed as described below. In order to denature and reduce the mAb samples, 1 μl of 1M DTT was added to 100 μl of 1 mg/mL mAb in 6M guanidine HCl and 100 mM Tris (pH 8.0) and incubated at 37° C. for 30 minutes. Subsequently, 5 μl of 0.5 M iodoacetic acid (IAA) was added to the reduced sample and 30-minute incubation at 37° C. was carried out for alkylation. A follow-up desalting step using Zeba desalt spin cartridges (Thermo Scientific, Rockford, Ill.) was performed to exchange into 10 mM Tris buffer (pH 8.0). Trypsin digestion was done at an enzyme/protein ratio of 1:20 at 37° C. for 1 hour, quenched with the addition of TFA, and analyzed on an Orbitrap Velos Ion Trap MS (Thermo Scientific, Waltham, Mass.) coupled to an Acquity capillary HPLC (Waters, Milford, Mass.). Peptides were resolved for introduction into the mass spectrometer with a Waters Acquity UPLC BEH Shield RP18, 1.0 mm×150 mm 1.7 μm reverse phase C18 column using a binary gradient with 0.02% TFA, 0.08% formic acid in water as MPA and 0.02% TFA, 0.08% formic acid in acetonitrile as MPB at a flow rate of 50 μL/min. The mass spectrometer was run in positive ion mode with a capillary voltage of 4.0 kV.

Although the DNA sequence of expression vector was routinely confirmed prior to the initiation of the cell line development campaign, sequence variants in low abundance may be undetectable due to the low sensitivity of the conventional Sanger sequencing method. To rule out the possibility that the single nucleotide mutation(s) observed in transfectants 11 and 27 arose from the minor contamination in the expression vector, the plasmid DNA stock was sequenced via DNAseq. None of the mutations observed via RNAseq were detected, suggesting that all three point mutations were introduced at either transfection or selection/amplification stages (data not shown).

Figure 20:
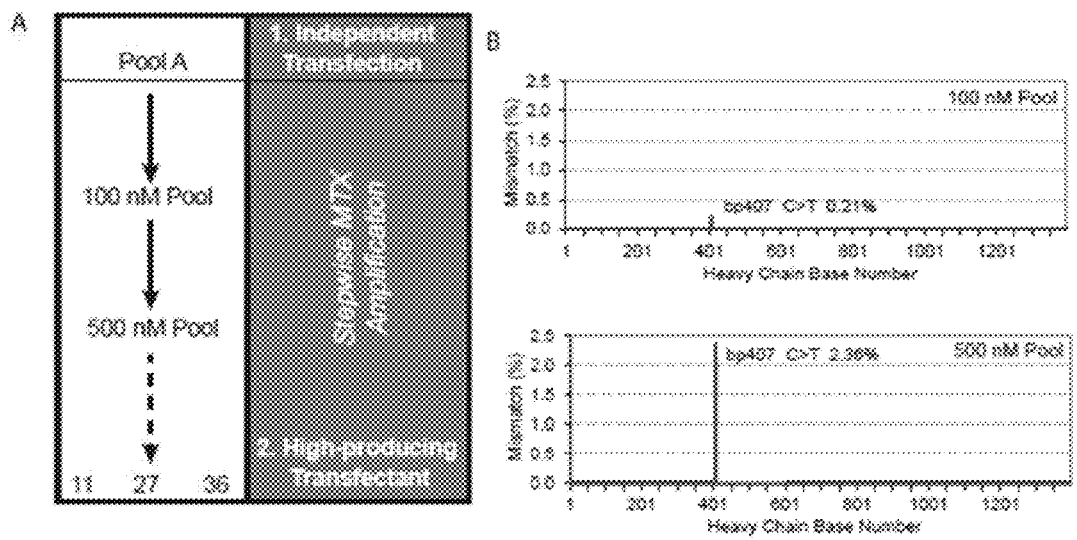
FIG. 20 shows results of RNAseq performed at two intermediate stages during stepwise MTX amplification to confirm the timing and mechanism of point mutation introduced in transfectants 11 and 27.

To further explore the timing of and mechanism of point mutation introduced in transfectants 11 and 27, RNAseq was performed for their parental pools at two intermediate stages during stepwise MTX amplification (FIG. 20A). A low level C/T mutation (0.22%) at 407 bp of the HC coding sequence was detected from the pool selected under 100 nM MTX, indicating that the particular mutational event occurred quite early in the cell line development process. Interestingly, we observed the same point mutation in the succeeding 500 nM pool at a much higher level of 2.6% (FIG. 20B). In contrast, the A/C point mutation at 132 bp of the LC coding sequence was detected in neither 100 nM nor 500 nM pool, suggesting that this mutation was likely elicited post-500 nM pool stage.

Although cell line development is traditionally a titer-driven process, critical protein quality attributes, such as sequence variants, are now taken into account as first-tier screening criteria during CLD to mitigate the risks of diminished safety and efficacy in biologics at late stage development and commercial manufacture. Many reports have shown that both DNA mutation and translational misincorporation can contribute to the presence of sequence variants in recombinant protein products (Feeney et al. 2013; Fu et al. 2012; Guo et al. 2010; Harris et al. 1993; Khetan et al. 2010; Ren et al. 2011; Wen et al. 2009; Yang et al. 2010; Yu et al. 2009; Zeck et al. 2012; Zhang et al. 2012). It becomes increasingly common to encounter heterogeneous CHO lines that produce low-level sequence variant(s) when highly sensitive analytical methods and advanced data analysis packages are available. In this example, more than 25% (i.e. 3 out of 11) high-producing lines analyzed showed genetic heterogeneity. Sequence variants are difficult to remove through downstream purification as they often retain overall physicochemical properties similar to the desired recombinant protein. Finding sequence variants existing in the drug substance would most likely result in restarting the CLD campaign which is costly and time-consuming. Therefore, early assurance of genetic homogeneity during CLD is essential. In this study, the elimination of transfectants 11 and 27 enabled us to prioritize the resources on mutation-free lines prior to the laborious cloning steps so as to reduce the risk of timeline delay. In addition, both transfectants 11 and 27 originated from transfection pool A whilst two other transfection pools, B and C, only delivered mutation-free transfectants, indicating that the mutations elicited at the transfectant level might be pool-dependent. We also scrutinized the high-producing clones and subclone that were derived from mutation-free parental transfectants to ensure their genetic homogeneity. The detection of the low level nonsense mutation in subclone 79-8-30, most likely conferred during subcloning, suggested the equal importance of RNAseq implementation at both early and late stages of CLD in that spontaneous or induced mutation may occur at any time during the cell line generation process. As a result, clone 36-17 but not subclone 79-8-30 was moved forward to process development despite their similar productivities.

Example 7

Detection of Alternative Splicing in a CHO Line D

The first few steps of analyzing alternative splicing by NGS are similar to those for the analysis of point mutations. The mapping of reads to reference sequence, filtering of mismatches for quality, end trimming of reads and tabulation of mismatches by position in the reference sequence are common to both analyses. The analysis then branches out to either detecting point mutations for the analysis of point mutations or to detecting alternative splicing for splicing analysis.

Figure 21:
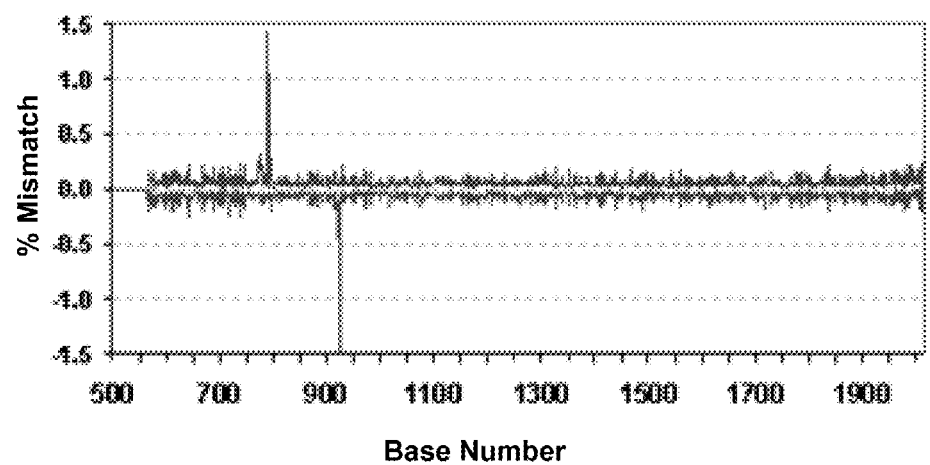
FIG. 21 shows overview of splice sites which shows mismatches as plotted by strand (Base numbers are relative to the reference sequence, and the green top strand peaks are splice donor candidate locations, while the red, bottom strand peaks are splice acceptor candidate locations).

For splicing analysis, the tabulated data are plotted as percent mismatch on the +/− strands without any additional filtering (FIG. 21). The resulting plot contains local regions of mismatch that are strand specific, which means lack of any counterpart on the opposite strand at the location. By contrast, point mutations are reported by reads from both strands and thus appear in the plot as paired peaks at the same location.

Unpaired (i.e., strand-specific) peaks in the plot may arise from at least two sources. The first source is artifacts resulting from limitation of the instrument and polynucleotide chemistry, which typically occur in a sequence specific manner. These mismatches often occur after short motifs (e.g. GGCNG), with a misincorporation event located within a few nucleotides 3' of the motif. These artifacts are usually located at a single base location and usually leave the surrounding sequence unaffected.

The second source of mismatches is insertion and deletion events ("indels"), which includes alternative splicing of mRNAs that are captured in the cDNA sequence data. When a cDNA fragment contains a splice junction, it no longer matches the reference sequence perfectly. As read data crosses the splice junction, the mapping software begins recording mismatches. When there are only a few mismatches, for example, at the end of a read, the mismatches are retained in the matching reads dataset, tabulated along with the other reads and plotted as described above.

Figure 22:
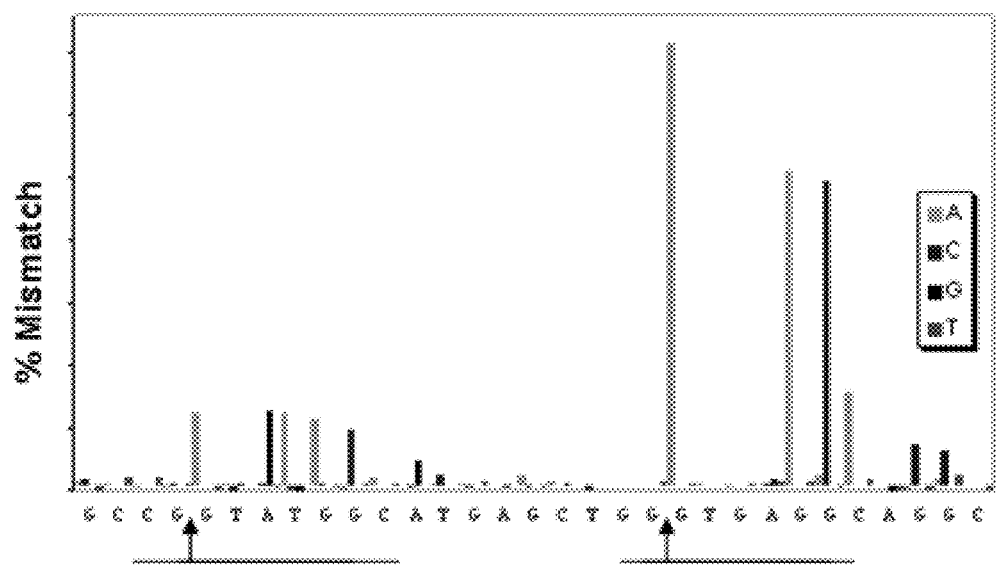
FIG. 22 illustrates two splice donor sites that are in close proximity (Donor motifs are underlined and the arrows show the exon/intron cleavage site, while mismatched bases are plotted using the color code in the legend).

The permissive parameters used during mapping of reads to reference sequence allow mismatches of 5-7 nucleotides of the read to be kept in the dataset. When plotted, the splice junction region appears as two regions of mismatch, one on the top strand as reported by top strand reads (FIG. 22) and the other on the bottom strand as reported by bottom strand reads. Mismatched bases shown in FIG. 22 are the downstream exon sequence at the junction after splicing has occurred. The top strand mismatch region is the (potential) splice donor while the bottom strand is the (potential) splice acceptor. Each region is a small cluster of 5-7 nucleotides that mismatch the reference sequence. This clustering of mismatches is distinct from point mutations and chemistry artifacts which are typically mismatched at a single nucleotide. Moreover, the donor and acceptor regions will also have some degree of conservation to the consensus splice donor and splice acceptor motifs.

In order to link the two candidate splice sites, the sequence at the junction including the mismatches is determined from the tabulated data at both sites. The two deduced sequences must overlap and make a consensus of the splice junction. The consensus sequence can then be used to search the original reads dataset for reads that span the junction but were rejected in the original mapping to the reference sequence. Using a 30-mer sequence, 15 nucleotides on either side of the junction, reads that confirm the splice junction can be identified and assembled into a consensus sequence.

The present disclosure is not to be limited in scope by the specific embodiments described herein. Indeed, various modifications of the invention in addition to those described herein will become apparent to those skilled in the art from the foregoing description and the accompanying figures. Such modifications are intended to fall within the scope of this disclosure and the claims.

REFERENCES

The contents of all cited references (including literature references, patents, patent applications, and websites) that may be cited throughout this application or listed below are hereby expressly incorporated by reference in their entirety for any purpose into the present disclosure. The disclosure may employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

1. Harris R J, et al. Nature Biotechnology 1993; 11: 1293-1297.
2. Wan M, et al. Biotechnology & Bioengineering 1999; 62: 485-488.
3. Dorai H, et al. BioProcess Internat 2007; 5: 66-75.
4. Wen D, et al. Journal of Biological Chemistry 2009; 284: 32686-32694.
5. Claverol S, et al. Molecular & Cellular Proteomics 2003; 2: 483-493.
6. Que A H, et al. BioProcess International 2010; 52-60.
7. Yu X C, et al. Analytical Chemistry 2009; 81: 9282-9290.
8. Wen D, et al. Journal of Biological Chemistry 2009; 284: 32686-32694.
9. Margulies M, et al. Nature 2005; 437: 376-380.
10. Shendure J & Ji H. Nature Biotechnology 2008; 26: 1135-1145.
11. Metzker M L. Nature Review 2010; 11: 31-46.
12. Victoria J G, et al. Journal of Virology 2010; 84: 6033-6040.
13. Shroder J, et al. PLoS ONE 2010; 5: 1-11.
14. McCulloch S D & Kunkel T A, Cell Research 2008; 18: 148-161.
15. Golberg A & Rubinsky B. Technology in Cancer Research and Treatment 2010; 9: 423-430.
16. Goulain M, et al. Proc. Natl. Acad. Sci. 1980; 77:1956-1960.
17. Martin S A, et al. EMBO Molecular Medicine 2009; 1: 323-337.

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

We claim:

1. A method for generating a production cell line capable of producing a protein, the method comprising:
   a) culturing a plurality of cells comprising a polynucleotide encoding the protein,
   b) sequencing the polynucleotide or a fragment thereof isolated from one or more of the cells,
   c) determining the percentage of sequence variants by comparing the sequence of the polynucleotide or fragment thereof obtained in step (b) with the known sequence of the polynucleotide or fragment thereof, and
   d) selecting and culturing cells having less than 2% sequence variants in the polynucleotide to generate a production cell line capable of producing the protein.

2. The method of claim 1, wherein the polynucleotide is selected from the group consisting of DNA, RNA, and a combination thereof.

3. The method of claim 1, wherein the sequencing in step (b) is performed by next generation sequencing (NGS) techniques.

4. The method of claim 3, wherein the sequencing in step (b) is performed by RNAseq.

5. The method of claim 3, wherein base callings of any variant on both strands of the polynucleotide are the same.

6. The method of claim 3, wherein each variant as determined in step (c) is 2 standard deviations above mean.

7. The method of claim 3, wherein end trimming is employed in step (c), the end trimming is based on the bias of variant frequency vs. read position.

8. The method of claim 3, wherein quality value filtering is employed in step (c).

9. The method of claim 3, wherein sequencing strand coverage is separated to discriminate sequencing error or to evaluate sequencing quality.

10. The method of claim 3, wherein cells having less than 1% sequence variants in the polynucleotide are selected and cultured to generate a production cell line.

11. The method of claim 3, wherein the polynucleotide is introduced into the plurality of cells by transfection prior to step (a).

12. The method of claim 3, wherein the polynucleotide is sequenced prior to being introduced into the plurality of cells.

13. The method of claim 1 further comprising a step of single-cell cloning after step (d) to generate a cell line derived from a single cell.

14. The method of claim 3 further comprising a step of culturing the selected cells of step (d) to produce the protein.

15. The method of claim 1, wherein the polynucleotide of step (b) comprises a cDNA molecule, and wherein the cDNA molecule is generated through reverse transcription of an mRNA molecule collected from the cells.

16. The method of claim 1, wherein sequencing in step (b) is performed by next generation sequencing (NGS) techniques and mass spectrometry.

17. The method of claim 1, wherein the culturing step (a) comprises amplification of the cells using a chemical selected from the group consisting of dihydrofolate reductase (DHFR), methotrexate (MTX), glutamine synthetase (GS), methionine sulfoximine (MSX), and a combination thereof.

18. The method of claim 17, wherein the culturing step (a) comprises at least two steps of amplification using MTX, the first step being conducted at a concentration of from 50 nM to 150 nM of MTX, the second step being conducted at a concentration of from 400 nM to 600 nM of MTX.

19. The method of claim 18, wherein the first step is conducted at a concentration of 100 nM MTX, and the second step is conducted at a concentration of 500 nM MTX.

20. The method of claim 18, wherein at least one clone producing the highest amount of the protein is selected after each of the first and second step.

21. The method of claim 20, wherein each selected clone is subject to sequencing to determine the percentage of sequence variants of the RNA in the clone.

22. A method for generating a production cell line capable of producing a protein, the method comprising:
 a) culturing a plurality of cells comprising an RNA molecule encoding the protein,
 b) sequencing the RNA molecule or a fragment thereof isolated from one or more of the cells,
 c) determining the percentage of sequence variants by comparing the sequence of the RNA or fragment thereof obtained in step (b) with known sequence of the RNA or fragment thereof, and
 d) selecting and culturing cells having less than 2% sequence variants in the RNA to generate a production cell line capable of producing the protein.

23. The method of claim 22, wherein the sequencing result from step (b) is further verified by mass spectrometry sequencing of the encoded protein.

24. The method of claim 22, further comprising a step (e) of identifying one or more mismatches caused by alternative splicing of the RNA.

25. The method of claim 24, wherein the mismatches caused by alternative splicing are strand specific mismatches.

26. The method of claim 24, wherein a cluster of mismatches comprising mismatches of between 5 and 7 nucleotides within a sequence window of 15 nucleotides are identified as mismatches caused by splice site and is kept in the matching data set.

* * * * *